(12) United States Patent
Judd et al.

(10) Patent No.: US 10,168,300 B2
(45) Date of Patent: Jan. 1, 2019

(54) MAGNETIC FLUX SENSOR QUALITY INDICATOR APPARATUS AND METHOD

(71) Applicants: Compagnie Generale des Etablissements Michelin, Clermont-Ferrand (FR); Michelin Recherche et Technique S.A., Granges-Paccot (CH); David Judd, Malden, SC (US); Frank E Gramling, Simpsonville, SC (US); Bradley D Schober, Greer, SC (US); Michael D Petrovich, Simpsonville, SC (US)

(72) Inventors: David Judd, Malden, SC (US); Frank E Gramling, Simpsonville, SC (US); Bradley D Schober, Greer, SC (US); Michael D Petrovich, Simpsonville, SC (US)

(73) Assignee: Compagnie Generale des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 15/324,917

(22) PCT Filed: Aug. 28, 2014

(86) PCT No.: PCT/US2014/053211
§ 371 (c)(1),
(2) Date: Jan. 9, 2017

(87) PCT Pub. No.: WO2016/032492
PCT Pub. Date: Mar. 3, 2016

(65) Prior Publication Data
US 2017/0227496 A1 Aug. 10, 2017

(51) Int. Cl.
*G01N 27/82* (2006.01)
*G01N 27/83* (2006.01)
(Continued)

(52) U.S. Cl.
CPC ............ *G01N 27/83* (2013.01); *G01M 17/02* (2013.01); *G01N 27/82* (2013.01); *B29D 30/54* (2013.01); *B29D 2030/546* (2013.01)

(58) Field of Classification Search
CPC ....... G01N 27/82; G01N 27/83; G01M 17/02; G01R 33/02; G01R 33/04; G01R 33/0011;
(Continued)

(56) References Cited

U.S. PATENT DOCUMENTS

| | | | | |
|---|---|---|---|---|
| 4,789,827 A | * | 12/1988 | Bergander | G01N 27/82 324/220 |
| 7,185,534 B2 | * | 3/2007 | Stoila | B29D 30/0061 73/146 |
| 2009/0237245 A1 | * | 9/2009 | Brinton | G07C 5/008 340/540 |

FOREIGN PATENT DOCUMENTS

| | | |
|---|---|---|
| EP | 2589959 A2 | 5/2013 |
| JP | 2009014678 A | 1/2009 |

(Continued)

OTHER PUBLICATIONS

International Search Report and Written Opinion for PCT/US16/53211 dated Sep. 11, 2015

*Primary Examiner* — Son T Le
(74) *Attorney, Agent, or Firm* — Neal P. Pierotti

(57) ABSTRACT

A flux leakage detection system and a method for providing a quality indicator for a flux leakage detection system are provided.

18 Claims, 20 Drawing Sheets

Tire and Sensor Drive

(51) Int. Cl.
*G01M 17/02* (2006.01)
*B29D 30/54* (2006.01)

(58) Field of Classification Search
CPC .......... G01R 33/0017; B29D 2030/546; B29D 30/54
See application file for complete search history.

(56) References Cited

FOREIGN PATENT DOCUMENTS

JP  2012237640 A  12/2012
WO  2013023818 A1  2/2013

\* cited by examiner

Sensor Head

Sensor Head with Cover

Ferrous Metal Flux Quality Indicator (FQI)

Sensor Inspection Device

Sensor Inspection Device

Sensor Inspection Device

Sensor Inspection Device

Ferrous Metal Flux Quality Indicator (FQI)

Ferrous Metal Flux Quality Indicator (FQI)

Ferrous Metal Flux Quality Indicator (FQI)

Sensor Inspection Device

Bead Sensor Device

MAGNETIC FLUX SENSOR QUALITY INDICATOR APPARATUS AND METHOD

TECHNICAL FIELD

The presently disclosed invention is generally directed to non-destructive testing methods and devices for tire casings. More particularly, the presently disclosed invention is directed to indications of quality for flux leakage detection systems that incorporate one or more sensors removably positioned relative to one or more tire surfaces.

BACKGROUND

When tires become worn, they may be restored with new tread bands or tread layers during a retread process. Retreading is a restoration or re-manufacturing process that not only extends the service life of the tires, but also is significantly less expensive than manufacturing new tires. Since recycling and retreading are key for reducing costs and energy inherent in the manufacturing of tire casings, an effective retread necessitates a tire casing with good structural integrity (i.e., without internal anomalies or irregularities).

Before replacing the tread, it may be advantageous to inspect the tire, including the reinforcement elements of the body ply, for damage or wear. In certain situations, inspection may reveal that replacement of the tire is required rather than retreading. Alternatively, repair of the tire may be required since not all damage to interior elements (e.g., the reinforcement elements of the body ply) is readily apparent from a visual inspection alone.

Prior and/or subsequent to retreading of a truck tire casing, one or more non-destructive testing (NDT) methods may be used to detect and locate internal anomalies. Such anomalies may include, but are not limited to, cracks, voids, delaminated layers and/or foreign material. Numerous attempts have been made using advanced NDT techniques, and several types of inspection procedures have been employed and commercialized by the tire remanufacturing industry.

As the reinforcement elements for commercial tires such as heavy truck tires are frequently constructed from a ferrous material, one or more sensors can be used to detect discontinuities in the reinforcement elements. In an exemplary configuration, an apparatus for detecting anomalies in a tire metallic cable may include a plurality of magnetic field sensors positioned along a common line and configured to produce individual electrical signals proportional to a sensed magnetic field. A magnet having north and south poles can be positioned to provide a magnetic field at each sensor parallel to the common line. The alignment of sensors and the magnet may be such that the flux lines from the magnet are generally parallel to the plane occupied by the sensors. A tire cable anomaly present between the sensors produces a detectable difference in signals produced thereby as a result of formation of perpendicular flux patterns produced by the anomaly. Such an apparatus and an exemplary method of use thereof is disclosed by co-owned and co-pending U.S. Ser. No. 13/260,744 for TIRE METALLIC CABLE ANOMALY DETECTION METHOD AND APPARATUS, filed 31 Mar. 2010, the entire disclosure of which is incorporated by reference.

Such sensor systems detect small amounts of magnetic flux leakage from a loss of cross sectional area of metallic tissue when such tissue is placed within the static magnetic flux field of the sensor system. The amount of flux leakage may be extremely small (e.g., on the order of 5 to 10 gauss), yet it must be detected within a static field of several hundred gauss. Several factors in the makeup of the sensor can influence the sensitivity of detection. For instance, there may be variability in the strength of the permanent magnets due at least in part to manufacturing differences. A reduction of strength over time may be due to shock, or there may be variability in the magnet joint. There may also be variability of the magnet's position with relation to a sensor array and/or variability of the sensor array position with relation to a contact cover of the sensor system. There may also be variability inherent in an individual flux sensor's sensitivity and linearity. It is also possible that the magnetic poles could be reversed in relation to the plurality of magnetic field sensors positioned along a common line. These and other variables make it necessary to ensure that each sensor system is constructed to within some tolerance of uniformity.

While there are commercially available gauss meters to measure flux density, such devices only address the issues of magnet strength and position. These devices disregard the sensitivity and position of each flux sensor. Such devices may also introduce inherent difficulty in repeating placement of the sensor such that two or more sensor systems may be compared to one another.

Therefore, reliable and cost-effective quality indicators for a flux leakage detection system are demanded that ensure repeatable and predictable positioning during data collection.

SUMMARY

The presently disclosed invention provides a flux leakage detection system. The presently disclosed flux leakage detection system includes a ferrous metal flux quality indicator (FQI) having an index incorporated between two opposed extents thereof. The index approximates an anomaly in metallic tissue and has a cross-sectional area to facilitate flux leakage from ferrous metal. The system also includes a sensor inspection device for detecting breaks in ferrous reinforcement elements during a tire inspection process. The sensor inspection device has a permanent magnet to create fields of magnetic flux used in detecting breaks in ferrous reinforcements during the tire inspection process. Movement of the FQI is effected such that, at the start of a test, the index is disposed between one magnetic pole of the magnet and one end of a sensor array of the sensor inspection device. Once data collection has started, the index is moved relative to the sensor array at a constant speed until the index is disposed between an opposite end of the sensor array and an opposite magnetic pole of the magnet. In some system embodiments, the sensor inspection device includes a body having an outermost inspection surface and one or more sensors selected from one or more of Hall Effect sensors, temperature sensors, optical sensors and any equivalent and complementary sensor thereof and any combination thereof.

In some system embodiments, the index includes at least one of one or more notches, grooves, apertures and slots integral with a surface of the FQI proximate the sensor inspection device during data collection. The index may be optionally coextensive with the opposed sides of the bar and approximately equidistant between the opposed extents of the bar. In some embodiments, the index may include at least one of a single notch of predetermined depth relative to a predetermined width and a predetermined length of the bar, with the predetermined depth being deep enough to provide a recognizable flux leakage wavelet; and an aperture extending through a predetermined thickness of the bar and optionally equidistant from opposed sides of the bar.

In some system embodiments, the FQI is fabricated as one of an essentially flat metal bar and a single strand cable that conforms to the outermost inspection surface of the sensor inspection device. When the FQI is fabricated as a bar, a predetermined length of the bar may be selected from a length equal to or less than a curvilinear distance between the two magnetic poles of the sensor inspection device; and a length sufficient such that, when at least a portion of the FQI is moved between opposed ends of an array of flux sensors of the sensor inspection device, neither opposed end of the FQI leaves a magnetic pole of the sensor inspection device.

In some system embodiments, one or more network-connected computing devices may be provided in communication with at least one of the FQI and the sensor inspection device. A platform may be provided that includes at least one of a server in communication with at least one network-connected device and an engine configured to perform at least one of recording test data as each sensor inspection device is tested; recording high peaks and low peaks of each sensor as the index is moved thereover; computing peak-to-peak response values as the index passes over each sensor; comparing a peak-to-peak response value of at least one sensor with at least one other peak-to-peak response value; and based upon the comparing, determining flux leakage integrity.

The presently disclosed invention also provides a method for providing a quality indicator for a flux leakage detection system. The presently disclosed method includes providing a flux leakage detection system as disclosed herein and moving the FQI such that, at the start of a test, the index is disposed between one magnetic pole of the magnet and one end of a sensor array of the sensor inspection device. Once data collection has started, the index is moved relative to the sensor array at a constant speed until the index is disposed between an opposite end of the sensor array and an opposite magnetic pole of the magnet.

Other aspects of the presently disclosed apparatus will become readily apparent from the following detailed description.

BRIEF DESCRIPTION OF THE DRAWINGS

The nature and various advantages of the presently disclosed invention will become more apparent upon consideration of the following detailed description, taken in conjunction with the accompanying drawings, in which like reference characters refer to like parts throughout, and in which.

DETAILED DESCRIPTION

The presently disclosed invention is directed to one or more methods, devices and systems for providing one or more equivalents of an image quality indicator (IQI) or Pie Gauge that can be used as a quality indicator for a flux leakage detection system. Inherent in the presently disclosed invention is a predetermined geometry and size of a ferrous metal flux quality indicator (FQI). Such qualities ensure repeatability and predictability of the methods of the FQI placement and motion during data collection as well as the accuracy and robustness of data analysis.

In the embodiments disclosed herein, the FQI may be significantly longer than the curvilinear distance between the two magnetic poles of a sensor system with which the FQI is employed. The FQI may be long enough such that when at least a portion thereof is moved between opposed ends of an array of flux sensors, the end of the FQI does not leave the opposite magnet pole.

Figure 1:
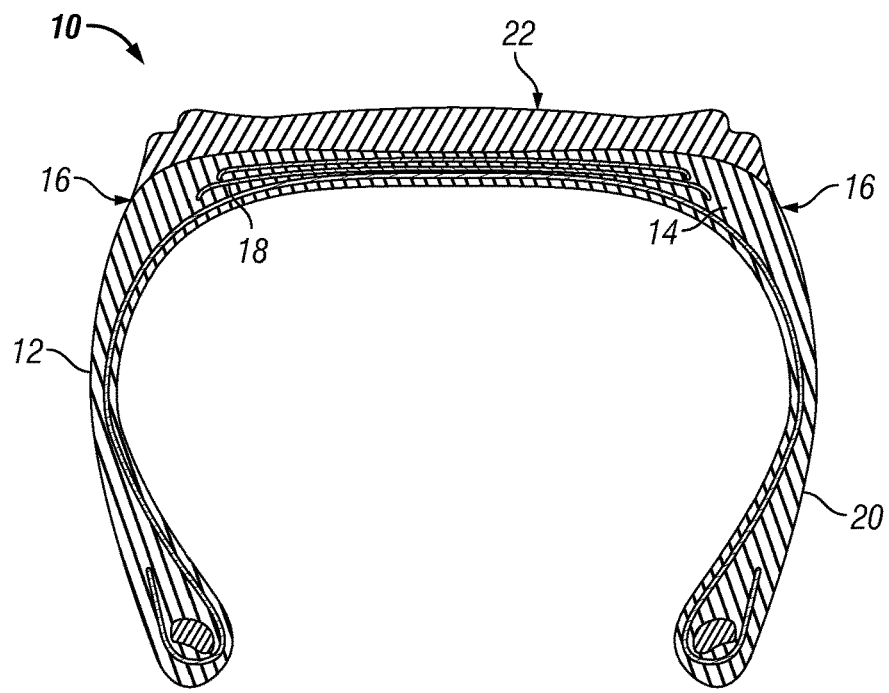
FIG. 1 shows a cross-sectional view of a representative tire.

Referring to the figures, wherein like numbers represent like elements, FIG. 1 shows an exemplary tire 10 that may be subject to inspection. Tire 10 has a tire casing 12 with a crown section 14, shoulders 16, reinforcement 18 and sidewall 20. Crown section 14 may have been buffed or otherwise worked to provide a prepared bonding surface to which a laterally extending tread 22 can be bonded (e.g., via one or more bonding layers). Buffing old tread off of the tire in preparation for retreading removes rubber that is typically replaced during the retreading process as part of the undertread portion of the tread that is bonded to the carcass. The material that is removed from the tire to be retreaded creates waste that is discarded and then replaced with new material that is bonded to the tire carcass during the retreading process. One or more tread elements (not shown) may be integral with tread 22 in a variety of configurations as known in the art. It is therefore understood that the configuration of tread 22 is not limited to that shown herein and that a variety of tread configurations are amenable for use with the carcass.

Figure 2:
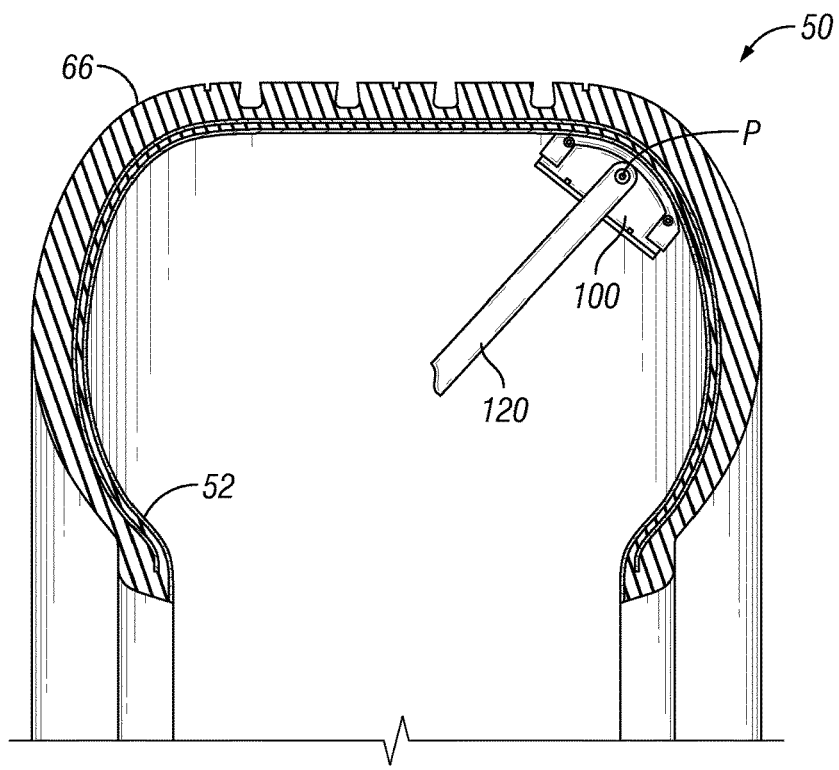
FIG. 2 shows a partial cross-sectional view of one side of a representative tire along with a side view of an exemplary sensor device with which the presently disclosed invention is employed.
Figure 3:
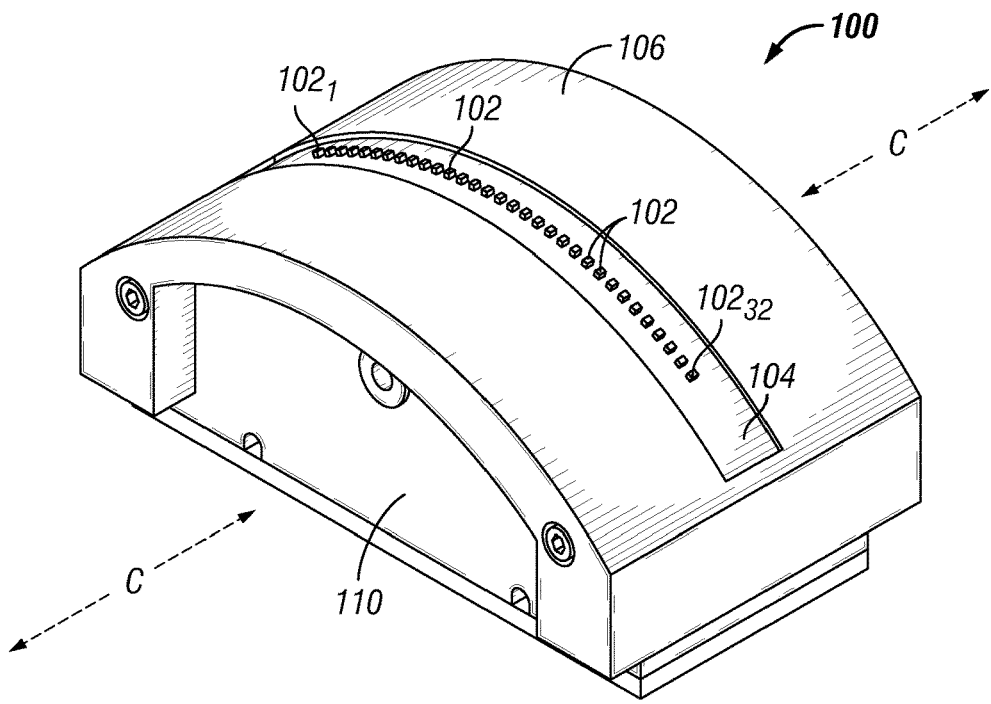
FIG. 3 shows a perspective view of a sensor head of the exemplary sensor device of FIG. 2.
Figure 4:
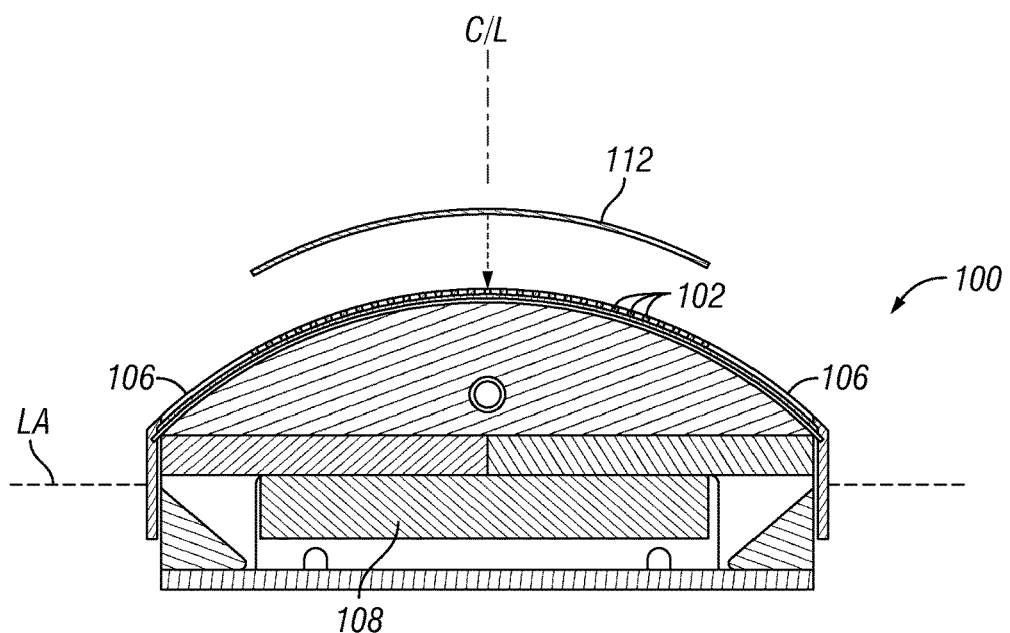
FIG. 4 shows a cross-sectional view of the sensor head of FIG. 3 with an optional cover therefore.

The presently disclosed FQI may be implemented with respect to one or more tire sensor devices and systems that are used for tire inspection. Referring further to FIGS. 2 to 4, an exemplary sensor device 100 is removably positioned with respect to a representative tire 50 for purposes of tire inspection. Such exemplary sensor device for use in tire inspection is disclosed by co-owned and co-pending PCT Appl. No. PCT/US2014/026097 for SENSOR DEVICE FOR TIRE INSPECTION filed 13 Mar. 2014, the entire disclosure of which is incorporated by reference herein. Sensor device 100 is useful for tire inspection particularly when it is desirable to position one or more sensors proximate an inner tire surface 52. For example, a body ply 54 may include reinforcement elements typically constructed from a ferrous material and embedded in the rubber materials used to construct tire 50.

As further shown in FIGS. 3 and 4, a plurality of sensors 102 may be arranged side-by-side or adjacent to one another along a generally longitudinal direction and upon a sensor support surface 104. Sensor support surface 104, which may be slightly recessed or positioned inwardly relative to an outermost inspection surface 106, may incorporate a printed circuit board or other substrate. As shown in this exemplary embodiment, sensor support surface 104 is generally parallel to inspection surface 106.

For this exemplary embodiment, sensors 102 may include Hall Effect sensors for detecting breaks in ferrous reinforcement elements. Hall Effect sensors may be employed that detect magnetic flux and provide a signal indicative of the presence of magnetic flux as well as the magnetic flux density. In some embodiments, thirty-two Hall Effect sensors may be used as indicated by sensors $102_1$ to $102_{32}$ of the array shown in FIG. 3. The use of multiple sensors ensures that at least one sensor 102 will be located on each side of a break as tire 50 is rotated during the inspection process. For detecting breaks in the reinforcements of body ply 54, the use of multiple sensors improves effectiveness of sensor device 100 in detecting breaks. As shown, a shoulder portion 66 of tire 50 is a high flexion zone for the tire and is therefore a location where breaks in reinforcement ply 54 are likely to be found. Although sensor device 100 is shown in use along a shoulder portion 66 of tire 50, use of the sensor device is not so limited. It is further understood that sensor device 100 can be useful for other tire inspections using other sensor types where placement of the sensor(s) in close proximity to the inner tire surface is desired, including instances where placement of one or more sensors along regions of tires of various sizes and profiles is desired. For example, sensor device 100 may include one or more of Hall Effect sensors, temperature sensors, optical sensors and/or any equivalent and/or complementary sensor thereof and any combination thereof.

When sensors 102 are Hall Effect sensors, sensor device 100 may be equipped with a permanent magnet 108 in order to create fields of magnetic flux used in detecting breaks in ferrous reinforcements. Magnet 108 may be integral with a body 110 of the sensor device (e.g., a compartment may be provided in body 60 into which the magnet is received). Sensor device 100 may also be provided with a protective cap 112 (see FIG. 4) to protect sensors 102 from being damaged during an inspection process (e.g., where tire 50 is rotated past sensor device 100). In this exemplary embodiment, magnet 108 is oriented with a longitudinal axis LA that is parallel to a line T that is tangent to an outermost detection surface of inspection surface 106 at the centerline C/L of sensor device 100.

Inspection surface 106 may incorporate a profile of an arc of a circle when viewed along the longitudinal-direction. The arc of this circle has a predetermined radius that is orthogonal to a circumferential direction of tire 50 when sensor device 100 is positioned against inner tire surface 52 as shown. This configuration allows sensor device 100 to be used over a wide variety of tire shapes and sizes since such profile allows the placement of sensors 102 in close proximity to inner tire surface 52 so that tire 50 can be properly inspected by a single rotation of the tire relative to the sensor device.

As shown, sensor device 100 is positioned along inner surface 52 by a positioning system that includes a support arm 120. Sensor device 100 is pivotally connected to a support arm 120 at point P that allows ready adjustment of the sensor device's orientation relative to the profile of inner tire surface 52. Support arm 120 does not form part of the presently disclosed invention and is provided by way of example only. It is understood that other positioning systems may be used with sensor device 100. The description of sensor device 100 and its operation provides background for this invention and does not form part of the presently disclosed invention.

It is further understood that representative tire 50 may be any representative tire, including a tire having a configuration as shown in FIG. 1, but not limited thereto. This is consistent with the understanding that certain embodiments of the sensor device are particularly suited for use along a shoulder portion of a variety of tire sizes of different widths and profiles, while other embodiments are suited for use along other tire portions. For example, complementary sensor devices and systems are disclosed by co-owned and co-pending PCT Appl. No. PCT/US2014/026021 for SENSOR DEVICE WITH MAGNET AND SENSOR ARRAY FOR TIRE INSPECTION filed 13 Mar. 2014, the entire disclosure of which is incorporated by reference herein.

Referring further to the figures, exemplary embodiments of the presently disclosed FQI are shown, each of which is useful with a sensor system and device such as shown with respect to FIGS. 2 to 4. The presently disclosed invention provides a simple and effective approach to validate the operability and correct assembly of sensor heads such as those shown herein. The utility of the presently disclosed embodiments is not limited to use with such illustrated sensor systems, and use of one or more of the disclosed embodiments may be amenable with differently configured sensor systems.

Relative motion should occur between the FQI and a sensor to be tested. In exemplary methods of FQI placement, movement is effected such that, at the start of a test, an index should be disposed between one pole of the magnet and the first sensor of the array. When using the presently disclosed FQIs, the selected FQI should be placed proximate the sensor with the index (e.g., one or more of a notch, aperture, slot, groove and the like provided on a surface of the FQI proximate to the sensor inspection device during data collection) just off an end of the sensor (e.g., a circumferential end of sensor 100 as shown herein) and placed as close as possible to the lateral middle of the sensor. Once data collection has started, the FQI index should be moved linearly relative to the sensor array with a relatively constant speed until the notch is disposed between the opposite end of the sensor array and the opposite pole of the magnet. This will result in a typical wavelet signature for each sensor. The wavelet will provide a positive spike followed by a negative spike. Which comes first—positive or negative—is a direct result of the poles of the magnet and the direction of relative motion. If either is reversed, the signature will change to a negative spike followed by a positive spike.

Data analysis involves the recording of high peaks and low peaks of each sensor as the notch is moved thereover. Each sensor signal may be analyzed algorithmically, for example, using a MATLAB routine developed to extract peak-to-peak values of the wavelets. It is understood that the data can be analyzed offline by any mathematical analysis tool (e.g., Matlab, Excel, etc.), or a program function may be executed. Each flux sensor's signal should be analyzed to find the peak-to-peak value of the response as the index passes over the sensor. This peak-to-peak value represents each sensor's full response to both sides of the index as it passes over the sensor. Because the sensor data collection system is based upon time, the slope of the wavelet is a result of the speed of relative motion between the FQI and the sensor. The algorithm does not require a consistent slope.

Figure 5:
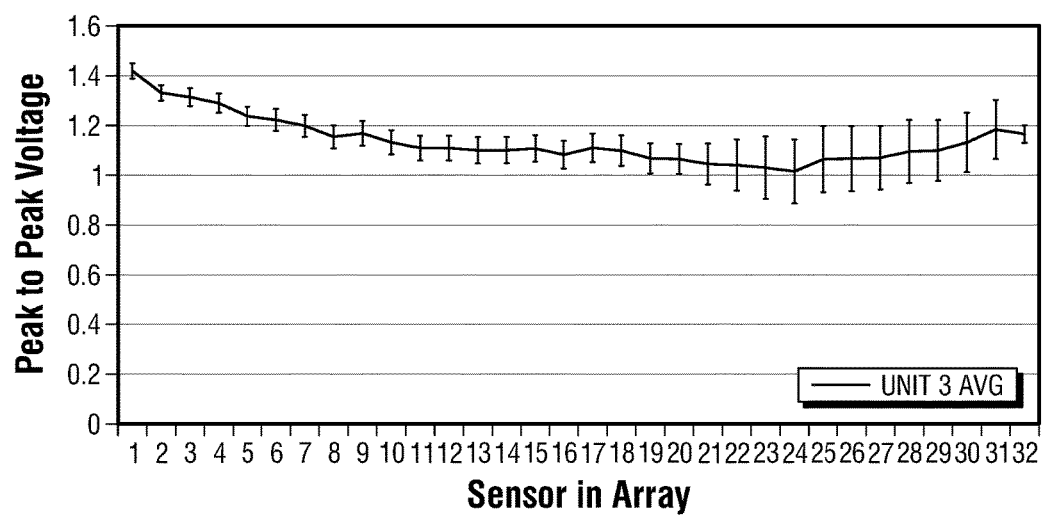
FIG. 5 shows exemplary results of tests wherein the peak-to-peak value for each sensor is averaged with respect to other repeat tests of that specific sensor and plotted.

Along one axis of comparison, each sensor's response to the notch is analyzed and compared to other flux sensors in the array. A second axis of comparison includes each flux sensor's response on one sensor system to the same flux sensor's response from another comparable sensor system of the same purpose (e.g., a bead head to a bead head, a small head to a small head, a large head to a large head, etc.). The peak-to-peak value of this waveform should be within some predetermined tolerance of the peak-to-peak value of other comparable sensor systems. To determine repeatability and overall quality of the FQI, multiple repeat tests may be performed and the peak-to-peak value of each sensor extracted for each pass of the FQI over the sensor. As shown in FIG. 5, an exemplary result of five repeat tests is depicted wherein the peak-to-peak value for each sensor is averaged with respect to other repeat tests of that specific sensor and plotted. The error bars indicate a range between the maximum and minimum peak-to-peak value obtained for that sensor.

Figure 6:
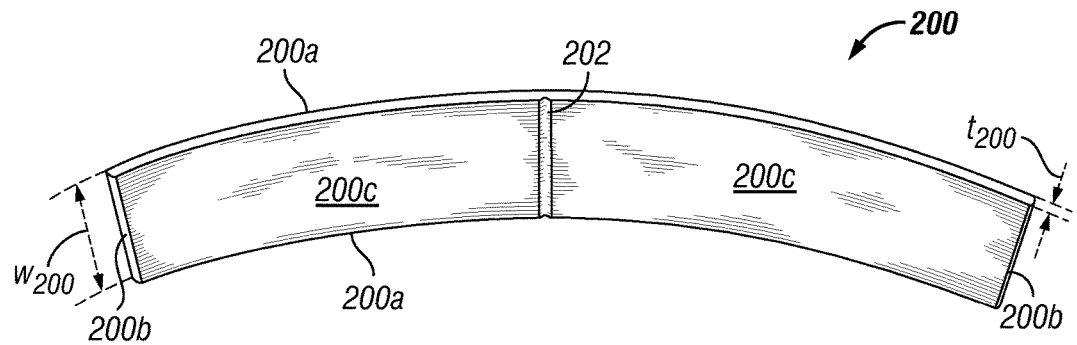
FIG. 6 shows a perspective view of an exemplary FQI as presently disclosed and FIG. 7 shows this FQI in use with an exemplary sensor inspection device.
Figure 7:
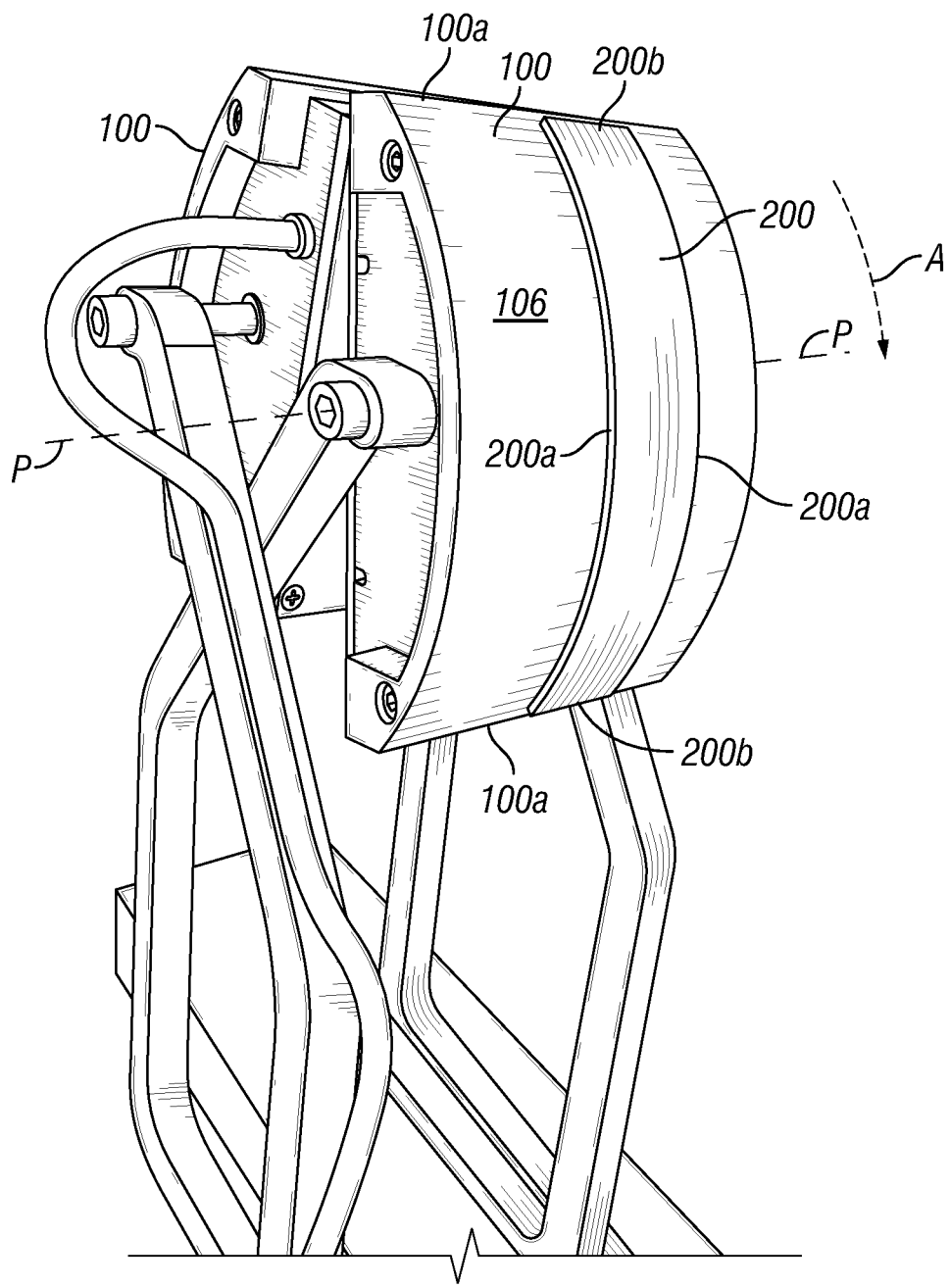

Referring particularly to FIGS. 6 and 7, an exemplary category of FQI embodiments incorporates a narrow metal bar with at least one index. Exemplary indices include one or more of notches, apertures, grooves and/or slots integral with a bar surface proximate a sensor array of a sensor device or system. Because a majority of flux passes through the metal, the index has (or the indices have) a cumulative cross-sectional area to facilitate flux leakage from the ferrous metal. That is, such an index should be deep enough to provide a recognizable flux leakage wavelet. An ideal wavelet is a positive and negative response, respectively, to the leading and trailing edge of an index (e.g., a notch, aperture, groove, slot or the like) passing over a sensor. Because it is advantageous to come close to the magnetic saturation point of the metal, in some embodiments, the index is about three quarters of the cross-sectional area of the metal. In this category of FQIs, the length and thickness of the FQI should be selected relative to the magnet size to ensure proper placement of the metal bar relative thereto. Improper placement of the bar may lead to disparate responses.

FIGS. 6 and 7 show an FQI fabricated from a metal bar 200 having a predetermined thickness $t_{200}$ and a predetermined width $w_{200}$. Bar 200 includes sides 200a of predetermined length coextensive with opposed extents 200b and delineating predetermined width $w_{200}$. Bar 200 may be fabricated from a ferrous material such as steel, or alternatively fabricated from a nonferrous metal. An index such as a single notch 202 may be provided along an inner surface 200c of bar 200 that approximates an anomaly in metallic tissue of a tire (although it is understood that two or more notches or equivalent structures may be employed as indices). Notch 202 may be coextensive with sides 200a and approximately equidistant between extents 200b. Notch 202 has a predetermined depth relative to the thickness of the material along the width $w_{200}$ of the bar and may be formed using a band saw or like device.

Bar 200 is fabricated as an essentially flat member and thereafter bent to a radius approximating the radius of an arc of a sensor device inspection surface (e.g., such as that shown with respect to sensor device 100 of FIGS. 2-4 and FIG. 7). The length of bar 200 should be sufficient to allow notch 202 to pass each sensor fully while opposed extents 200b remain on the outboard side of the magnets. In the exemplary embodiment shown in FIGS. 6 and 7, bar 200 has a length such that opposed extents 200b are generally coextensive with corresponding extents 100a of a sensor device 100 (and more particularly extents of inspection surface 106 thereof). In the case of plate steel, the surface of the plate should be sufficiently smooth to encumber leakage flux at any area other than the index (i.e., the notch, groove, aperture and/or slot).

In a method of FQI placement and motion, upon initiation of a test of flux quality, notch 202 should be between one pole of the magnet and a first sensor of a sensor array. Once data collection has started, notch 202 should be moved curvilinearly along the sensor array until notch 202 is disposed between the opposite end of the sensor array and the opposite pole of the magnet. During testing, bar 200 is disposed initially with an inside surface 200c (and therefore notch 202) thereof adjacent a sensor inspection surface 106 as depicted in FIG. 7. The notch is initially placed off of the sensor face. Upon initiation of data acquisition, bar 200 is slowly slid down across all sensors in a radial direction (e.g., as indicated by arrow A in FIG. 7). Upon passing notch 202 across all sensors in the array, data collection is halted. This entire process is then repeated for at least a second sensor face. Each sensor signal is evaluated for peak-to-peak value as notch 202 passes over each respective sensor. Data analysis involves the recording of the high peak and the low peak of each sensor as notch 202 passes thereadjacent. The peak-to-peak value of a resulting waveform should be within a predetermined tolerance of the peak-to-peak value of other qualified sensor systems.

Figure 8:
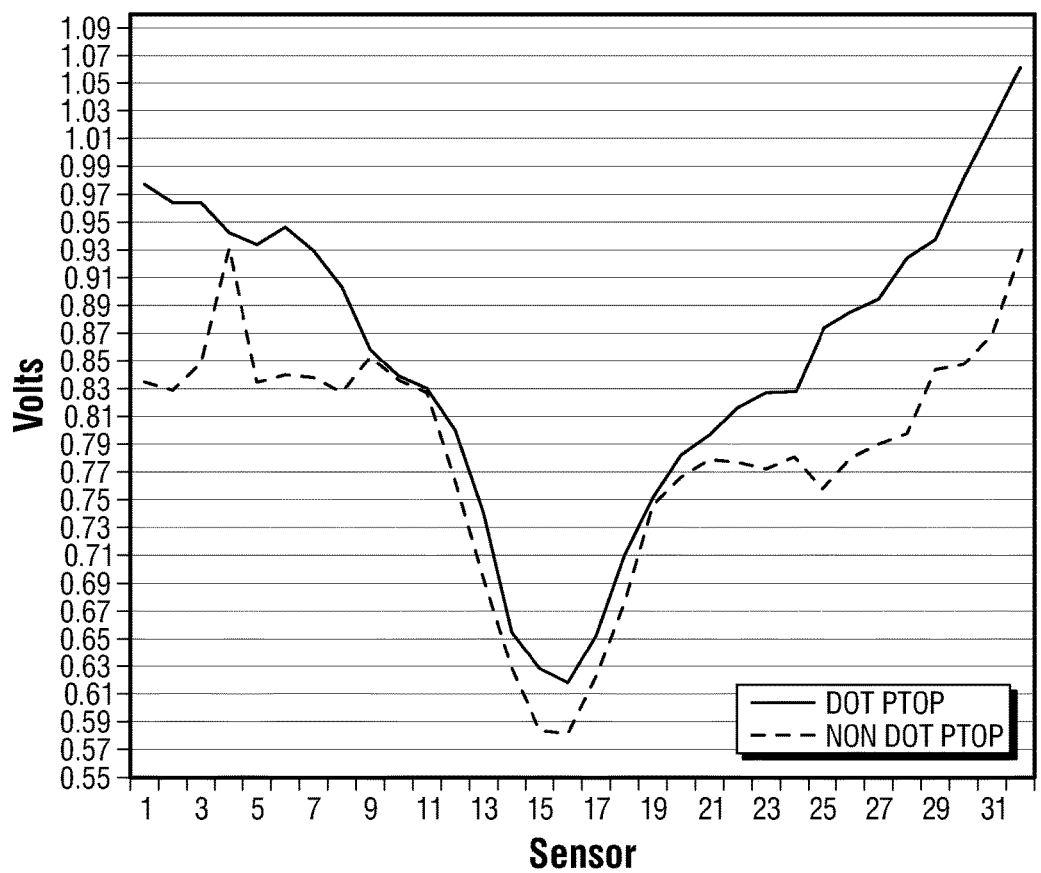
FIGS. 8 to 10 show exemplary comparisons of peak-to-peak values as the index of the exemplary FQI of FIG. 6 passes over a respective sensor of the exemplary sensor inspection device.

An exemplary comparison of such peak-to-peak values is depicted in FIG. 8. Such exemplary data depicts an interesting shape of peak-to-peak values (e.g., high on the array ends and low in the middle of the array). Such phenomena may be attributable to the relatively short test apparatus, the ends of which did not remain in close proximity to the magnet poles during the relative motion. "DOT" and "Non DOT" assignations refer to testing on two sensors wherein one sensor is disposed on a side of a tire's DOT stamp. It may be desirable to conduct testing with a pair of sensor devices 100 spread from each other, as testing with the devices in close proximity may cause some uneven influence from the heads of immediately adjacent sensor heads. Variability from run to run may be proportional to the size of the signal.

Example

Figure 9:
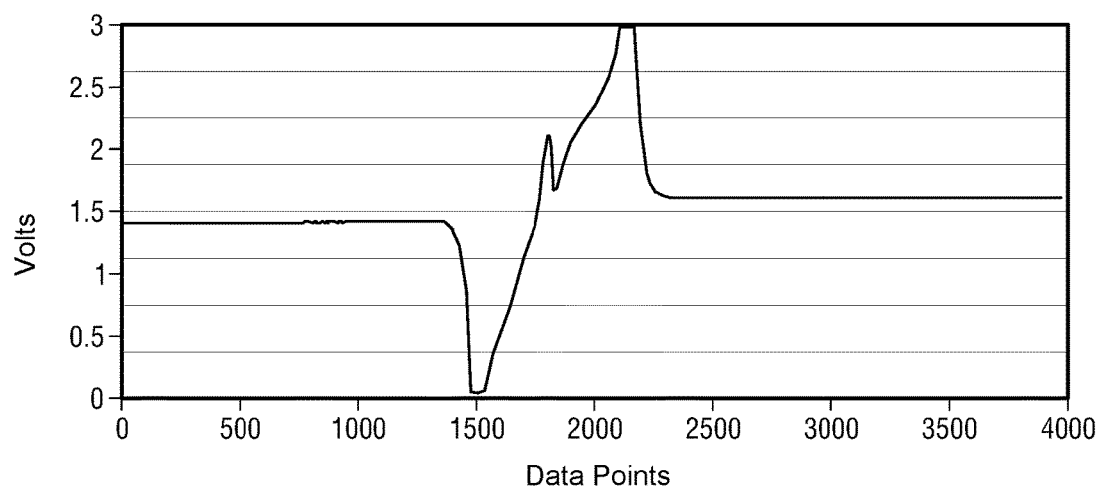
Figure 10:
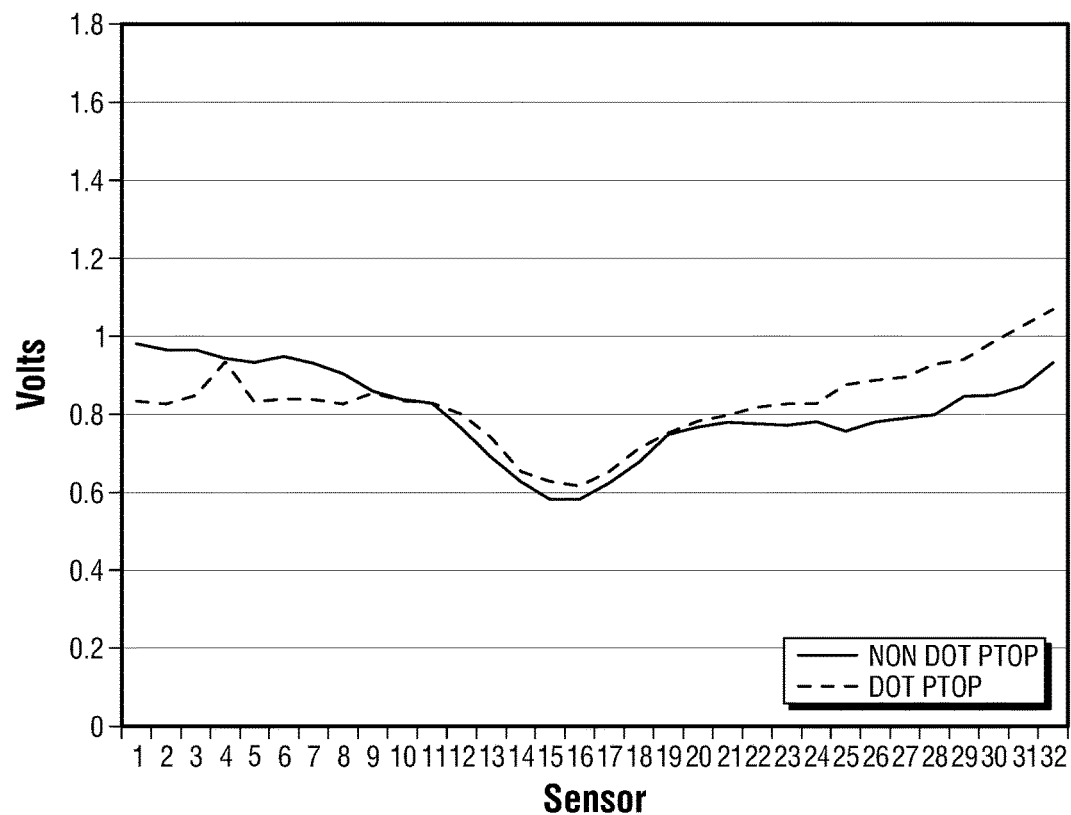

An FQI is provided as a bar with a notch wherein the bar and the notch have the following parameters:
Bar Dimensions: 17.59 mm wide×1.85 mm thick×113 mm long.
Notch Dimension: 0.61 to 0.95 mm deep×1.5 mm×full bar width
Cross-sectional area of Notch: 42.2%. This area is expressed in terms of a percentage because the amount of flux leakage is dependent more on the reduction of a good flux conduction area than on straight physical dimensions. The percentage is derived from first taking the average notch dimension which would be the average of 0.61 mm and 0.95 mm ((0.61 mm+0.95 mm)/2) which is 0.78 mm. In other calculations disclosed herein there are not two notch dimensions but instead only one so an average depth does not need to be calculated. This depth is then multiplied by the width of the notch (0.78 mm×17.59 mm) to yield 13.72 mm squared. This number is then divided by the bar dimensions (17.59 mm×1.85 mm) of 32.54 mm squared to get the cross-sectional area as a percentage. This percentage is thus (13.72 mm squared/32.54 mm squared) 42.2%. The other cross-sectional areas of the notch and slot discussed herein can be calculated in the same manner to yield the noted percentage.
Average Peak to Peak Amplitude: 0.828 volts
Because of the short sides on either side of the notch, the opposed extents of the bar completely leave the poles of the magnet. This causes a very different wavelet to be produced. The correct wavelet is the smaller signature inside of the larger signature (see FIG. 9). When the wavelet is manually extracted, the result indicates a large difference from sensor to sensor in the same array with stronger responses at the extreme ends of the array and magnet poles (see FIG. 10). This may indicate a need to degauss the steel bar prior to testing. Also, the large difference between each end of the sensor array may be attributable to a difference in the magnet position. The difference between the middle sensors meanwhile may be a difference in "height" of the sensor array or overall strength difference of the magnets.

Figure 11:
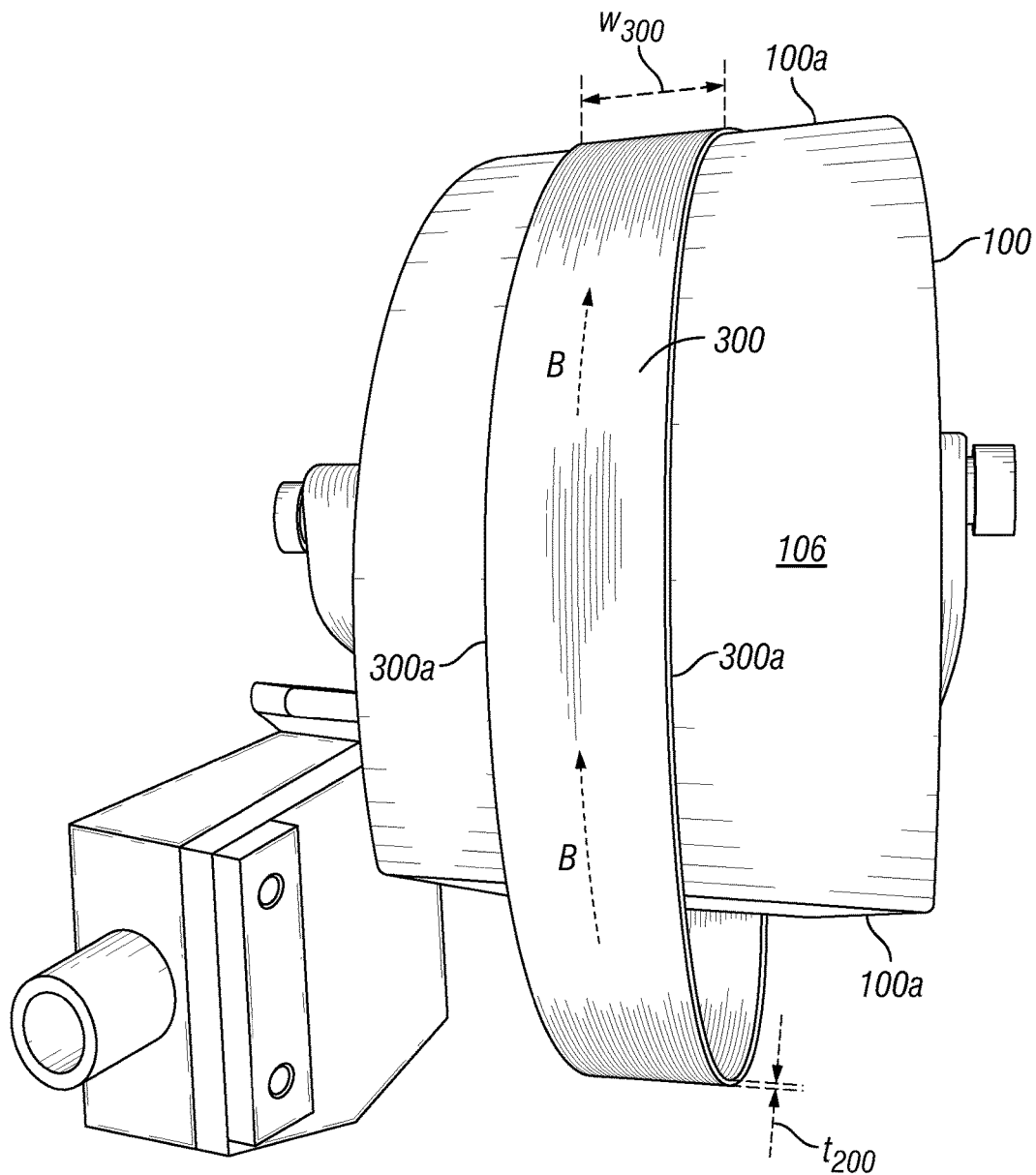
FIGS. 11 and 12 show respective top perspective and side perspective views of another exemplary FQI as presently disclosed in use with an exemplary sensor inspection device.
Figure 12:
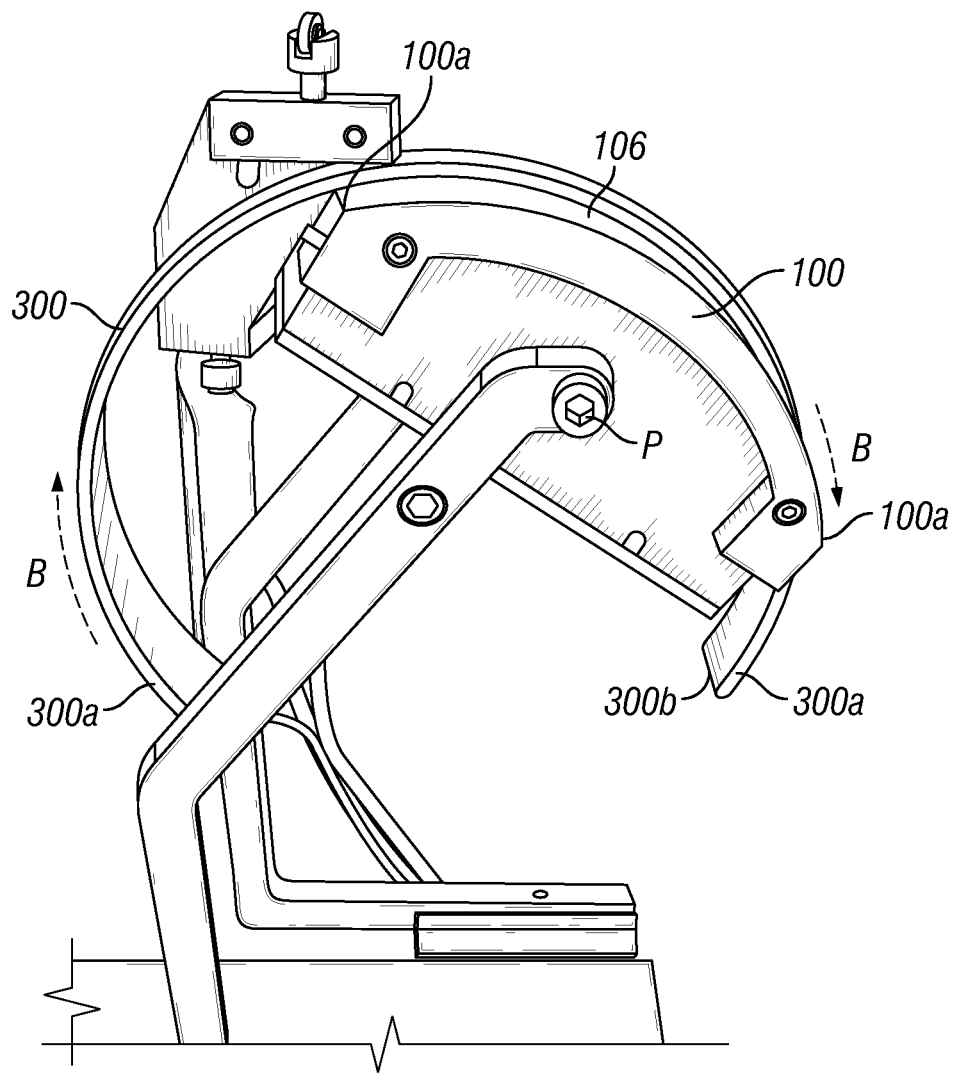

As shown in FIGS. 11 and 12, another exemplary FQI in this category is provided that includes a large flat bar 300 fabricated from a ferrous material such as steel (or alternatively fabricated from a nonferrous metal). Bar 300 has a predetermined thickness $t_{300}$ and a predetermined width $w_{300}$. Bar 300 includes sides 300a of predetermined length coextensive with opposed extents 300b and delineating predetermined width $w_{300}$. Bar 300 may be fabricated as an essentially flat member and thereafter bent to a radius approximating the radius of an arc of a sensor device inspection surface (e.g., such as shown with respect to sensor device 100 in FIGS. 11 and 12). The length of bar 300 should be of sufficient length to allow extents 300b to approach one another yet remain adjacent the sensor array during testing (i.e., to allow the FQI to "self-center" on the magnetic poles in the width direction). That is, the length should be sufficiently long enough to remain in close proximity to the magnet poles during the entire relative motion required by the data collection method. Upon initiation of data acquisition, bar 300 is slowly slid across all sensors in a radial direction (e.g., as indicated by arrows B in FIG. 11). This will provide a recognizable wavelet and reduce variability from sensor to sensor in the same array.

Example

Figure 13:
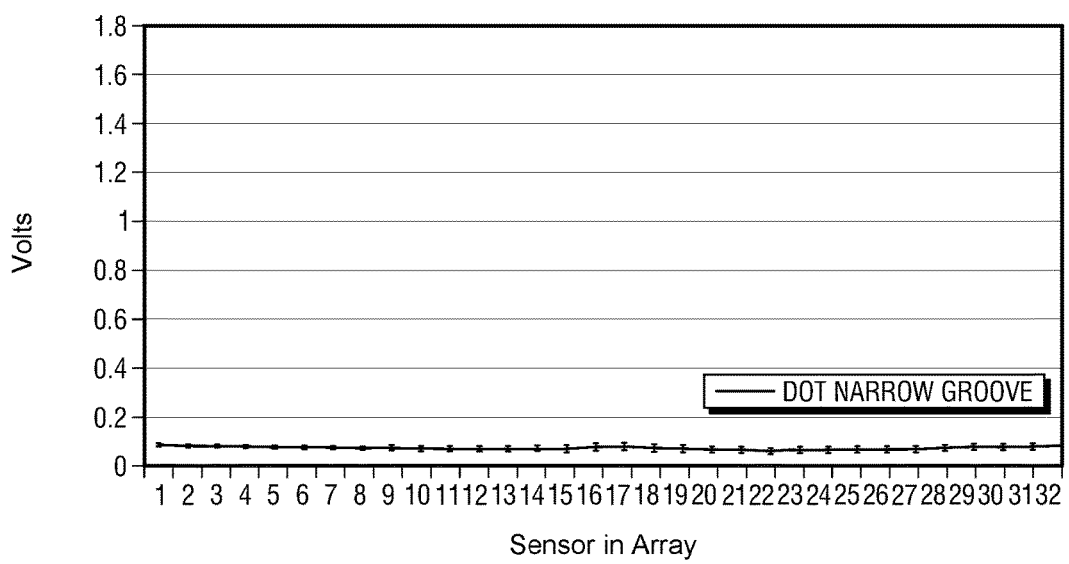
FIGS. 13 to 16 show exemplary comparisons of peak-to-peak values as the index of the exemplary FQI of FIGS. 11 and 12 passes over a respective sensor of the exemplary sensor inspection device.

An FQI is provided as a bar with a notch wherein the bar and the notch have the following parameters:
Bar Dimensions: 19.5 mm wide×1.88 mm thick×350 mm long.
Notch Dimension: 0.35 mm deep×1 mm×full bar width
Cross-sectional area of Notch: 18.5%
Average Peak to Peak Amplitude: 0.070 volts
Average Peak to Peak run to run variability: 0.019 volts
Before placing a notch in bar 300, several tests are performed to assess a variety of test conditions. In one test, lateral movement of bar 300 back and forth across sensor device 100 is effected to observe the effect of bar extents 300b leaving the magnetic field. In another test, bar 300 was centered laterally and radially with respect to sensor device 100. Bar 300 remained stationary while sensor device 100 was rotated along its mounting pins. In a third test, the effect of radial movement alone may be assessed without placement of a notch in the bar. As shown in FIG. 13, the data indicates very little effect from surrounding ferrous components.

Figure 14:
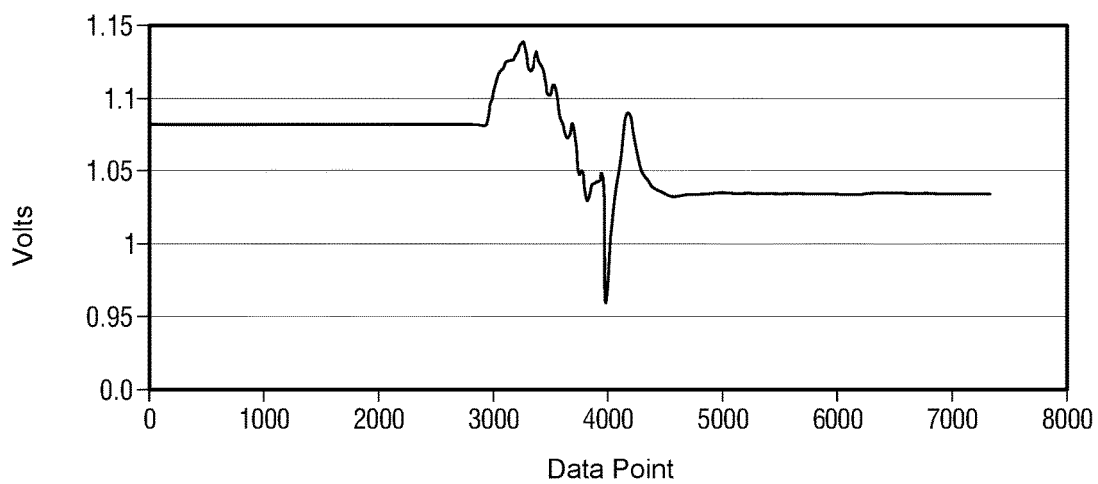

These tests were repeated after putting a notch in bar 300 generally at a midsection thereof. The notch was repeatedly positioned atop the sensor array proximate one extent of the array (e.g. adjacent sensor 0) and moved radially in a direction until the notch approaches the bottom of the sensor array (sensor 31) (e.g., movement is effected in the direction of arrow B as shown in FIG. 11). As depicted in FIG. 14, a repeatable waveform shape emerges.

An algorithm was developed (e.g., via Matlab or comparable software or tool) to automatically determine peak-to-peak values of the notch waveform. The excessive variability of peak-to-peak values may occur if the bar has a relatively narrow width that causes extents 300b to come off of the magnetic poles long enough to cause significant variation in peak-to-peak notch values. Alternatively, variability in the depth, width and/or edge shape of the notch may cause variation of leakage flux. Using longer ends on either side of the notch greatly improved the variability from sensor to sensor. The wavelet was not very pronounced and difficult to extract programmatically. The positive spike is barely recognizable. It may be overpowered by the magnetic signature imparted to the apparatus by the magnet poles. A deeper notch with more leakage may be needed to provide a stronger, more recognizable wavelet. Repeatability is good.

Example

Figure 15:
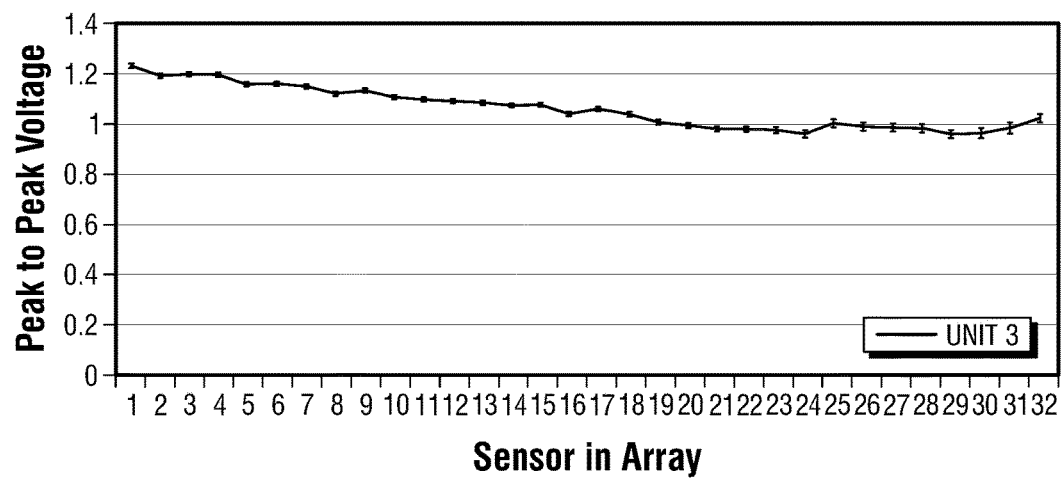

An FQI is provided as a bar with a notch wherein the bar and the notch have the following parameters:
Bar Dimensions: 19.5 mm wide×1.88 mm thick×350 mm long.
Notch Dimension: 0.95 mm deep×1.25 mm×full width of bar
Cross-sectional area of Notch: 50.5%
Average Peak to Peak Amplitude: 1.054 volts
Average Peak to Peak run to run variability: 0.022 volts
Multiple runs were performed on different sensor devices. Several attempts at collecting "bad" data were attempted with a spare sensor device to further test the repeatability. Data depicted in FIG. 15 was collected by purposefully starting with the FQI off-center from the sensor array and letting the FQI "automatically" center to the magnets as it moved relative to the sensors. The repeatability of this test was good except for sensors 22 through 27. This was traced to only one run having abnormally low data for those sensors only. It is noted that the higher order sensors were presented to the notch at the beginning of the test motion. Further data depicted in FIG. 15 was collected by flipping the FQI around every test. Repeatability is good in the center of the array, but on the edges it is large. It appears that the magnetic pole signature on the apparatus has an effect on the amplitude of the result. The end sensor peak-to-peak amplitudes alternated test to test, causing a high repeatability value.

Figure 16:
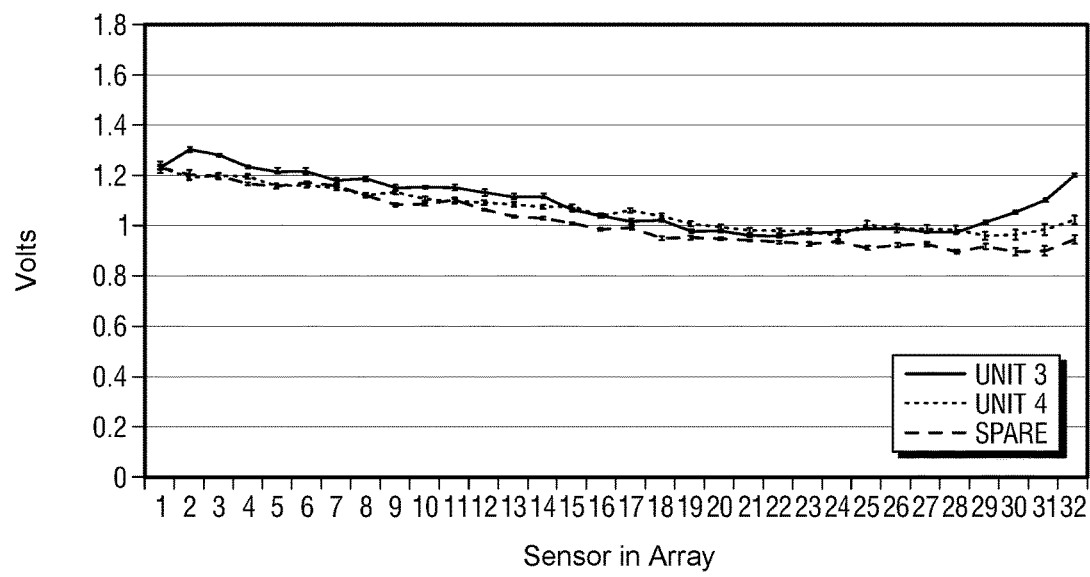

As shown in FIG. 16, the amplitude from this FQI was high. One of the end sensors was deflected past the low voltage rail as indicated by the flat spot on the bottom of the wavelet.

Figure 17:
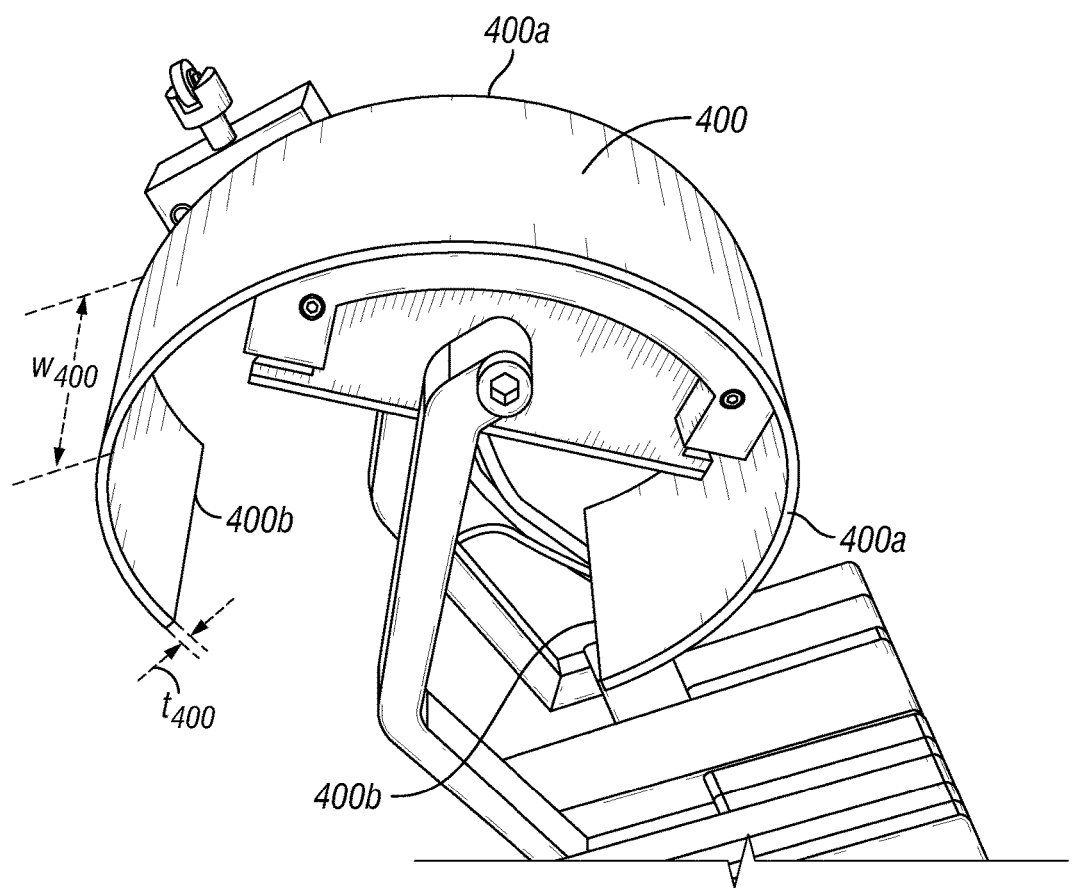
FIG. 17 shows a side perspective view of another exemplary FQI as presently disclosed in use with an exemplary sensor inspection device.
Figure 18:
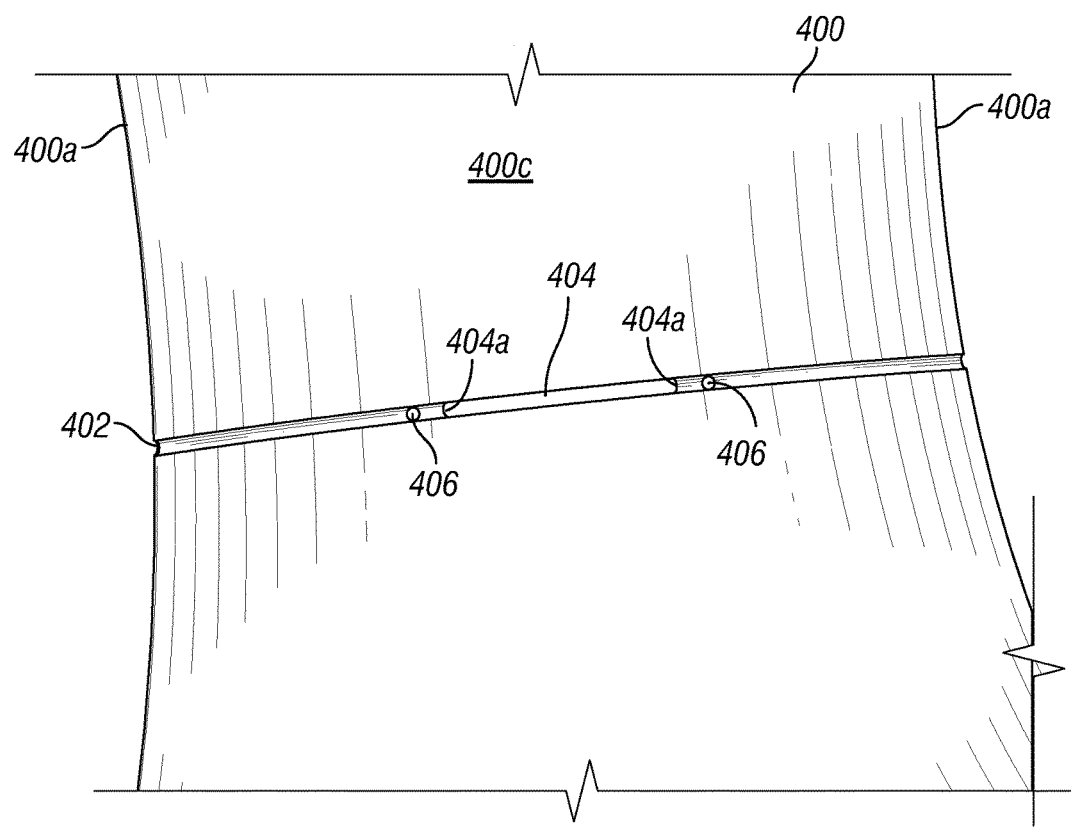
FIG. 18 shows a partial view of the FQI of FIG. 17 having an exemplary index including a notch and an elongate aperture.

Now referring to FIGS. 17 and 18, another exemplary category of FQI embodiments is provided that includes a wide plate fabricated from a ferrous material such as steel (or alternatively fabricated from a nonferrous metal). In the exemplary embodiments shown in FIGS. 14 and 15, a plate 400 has a predetermined thickness $t_{400}$ and a predetermined width $w_{400}$. Plate 400 includes sides 400a of predetermined length coextensive with opposed extents 400b and delineating predetermined width $w_{400}$. Plate 400 may be fabricated as an essentially flat member and thereafter bent to a radius approximating the radius of an arc of a sensor device inspection surface (e.g., such as shown with respect to sensor device 100 in FIG. 17).

As particularly shown in FIG. 18, an inner surface 400c of plate 400 (i.e., a surface adjacent sensor device 100 as shown in FIG. 17) may have a notch 402 defined thereon. As shown in FIG. 18, notch 402 may be located anywhere along a length of inner plate surface 400c and has a notch length coextensive with predetermined plate width $w_{400}$. An elongate aperture 404 is cut through plate 400 such that aperture 404 is equidistant from sides 400a. Aperture 404 has opposed extents 404a proximate each of which is provided a generally cylindrical aperture 406. Aperture 404 is of uniform geometry to ensure test integrity and accuracy of acquired data. Because the plate is wide and the notch and/or aperture covers the entire width, the apparatus is forgiving in the placement along the width axis of the sensor system. In some embodiments, the notch and/or aperture is about three quarters of the cross sectional area of the metal.

Figure 19:
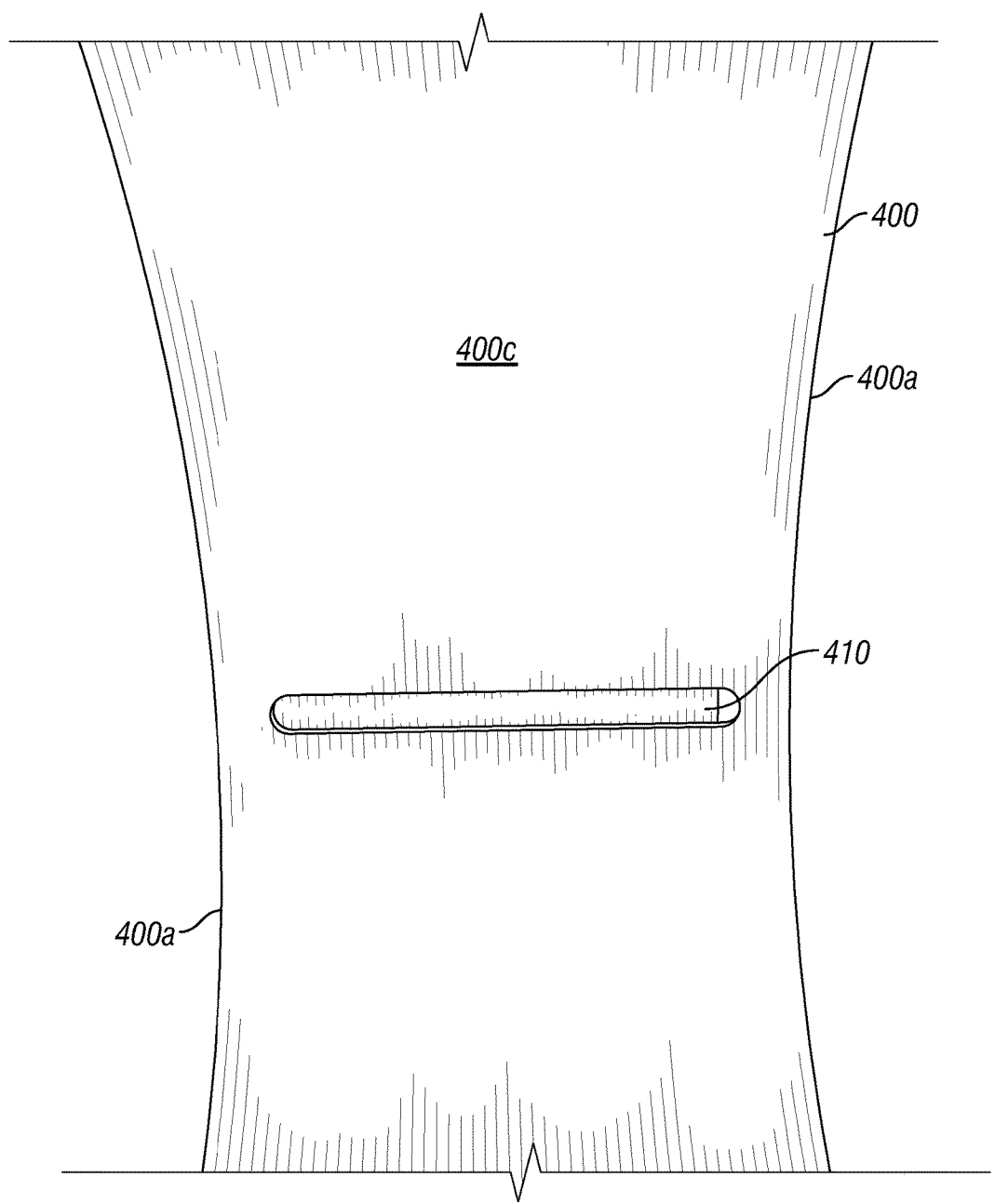
FIG. 19 shows a partial view of the FQI of FIG. 17 have an exemplary index including a single milled slot.

It is understood that other exemplary FQIs in this category may include a wide plate comparable with plate 400 shown in FIGS. 17 and 18 and having at least one aperture provided along a curved length thereof and equidistant along the predetermined width thereof. In some embodiments, the aperture may be provided as a single milled slot of variable length, such as milled slot 410 shown in an alternative exemplary embodiment in FIG. 19.

Example

Figure 20:
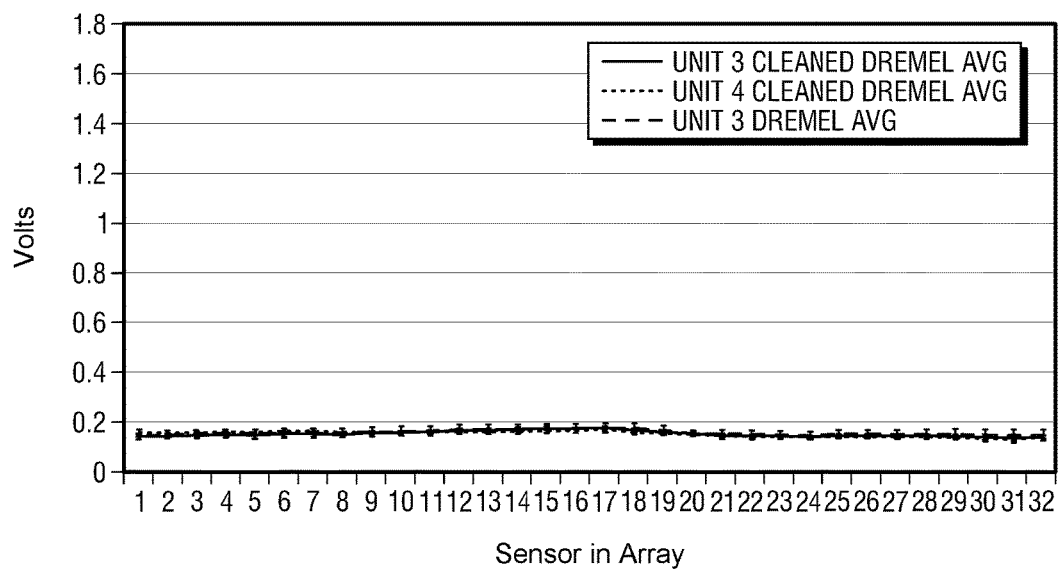
FIGS. 20 and 21 show exemplary comparisons of peak-to-peak values as an index of the exemplary FQI of FIG. 17 passes over a respective sensor of the exemplary sensor inspection device.

An FQI is provided as a wide plate with a notch and an aperture, wherein the plate, the notch and the aperture have the following parameters:
Bar Dimensions: 62.8 mm wide×1.87 mm thick×348 mm long.
Notch Dimension: 0.44 mm to 0.77 mm deep×1.00 mm×full bar width
Aperture Dimension: 15.25 mm long×1.4 mm Cross-sectional area of Notch and Aperture: 56.6%
Average Peak-to-Peak Amplitude: 0.158 volts
Average Peak-to-Peak run to run variability: 0.018 volts A measurable improvement on variability due to lateral movement is seen with a wide plate. Therefore, repeatability of this FQI is good, as is the wavelet produced by the finished FQI. Though the reduction in cross-sectional area is similar to the narrow band, the leakage is much less on this wider FQI (see FIG. 20). This is likely due to not fully saturating the steel with the magnets of the sensor device.

Example

Figure 21:
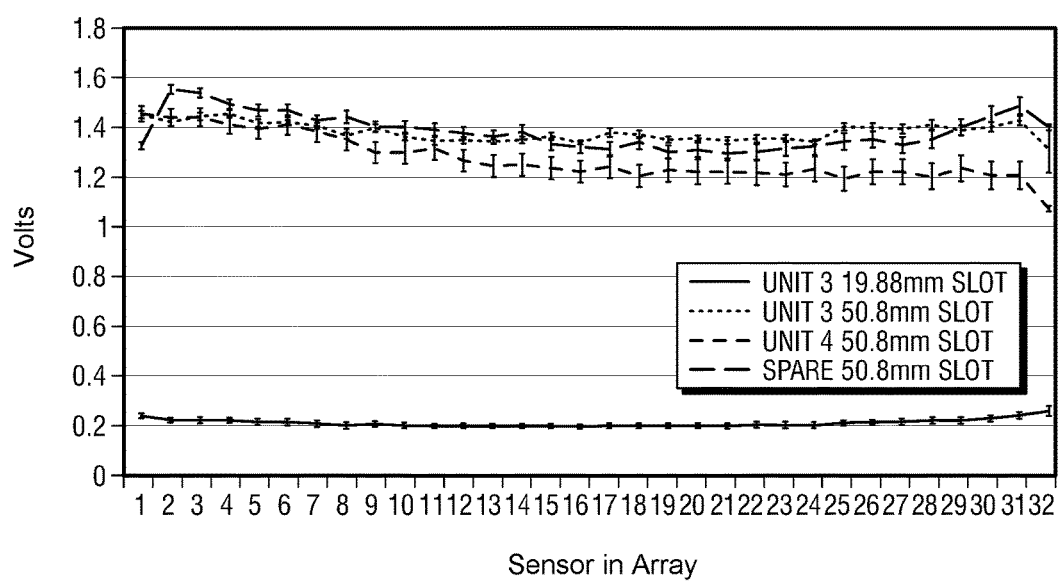

An FQI is provided as a wide plate with a milled slot. The milled slot is amenable to having variable dimensions. The plate and the slot have the following parameters:
Bar Dimensions: 62.39 mm wide×2 mm to 2.24 mm thick×348 mm long.
Initial Slot Dimension: 19.8 mm×4.0 mm
Enlarged Slot Dimension: 50.8 mm long×4.0 mm
Cross-sectional area of initial slot: 38.9%
Cross-sectional area of enlarged slot: 81.5%
Average Peak-to-Peak Amplitude of first slot: 0.204 volts
Average Peak-to-Peak run-to-run variability of first slot: 0.029 volts
Average Peak-to-Peak Amplitude of enlarged slot: 1.38 volts
Average Peak-to-Peak run-to-run variability of enlarged slot: 0.033 volts Repeatability with the shorter slot was good but became worse when the slot was widened (see FIG. 21). This could be due to several factors. A wider plate (i.e., more steel) is likely not saturated completely by the magnets of the sensor device. With lack of saturation, if the bar is passed slightly off-center, more or less flux may pass through the solid portion of the plate at the ends of the slot. This variance may cause a change in flux leakage over the sensors.

Figure 22:
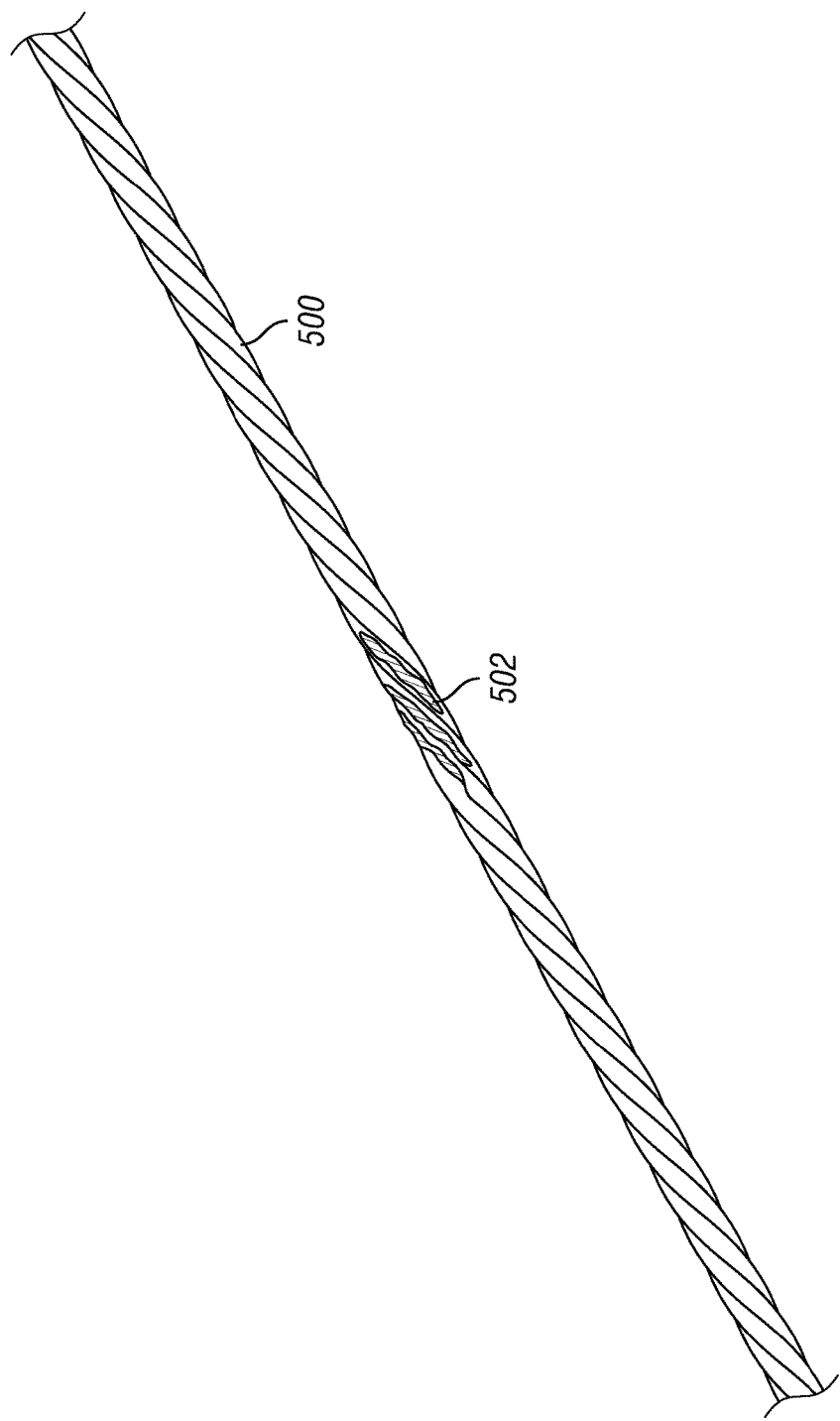
FIG. 22 shows a top partial perspective view of an exemplary FQI as disclosed herein.
Figure 23:
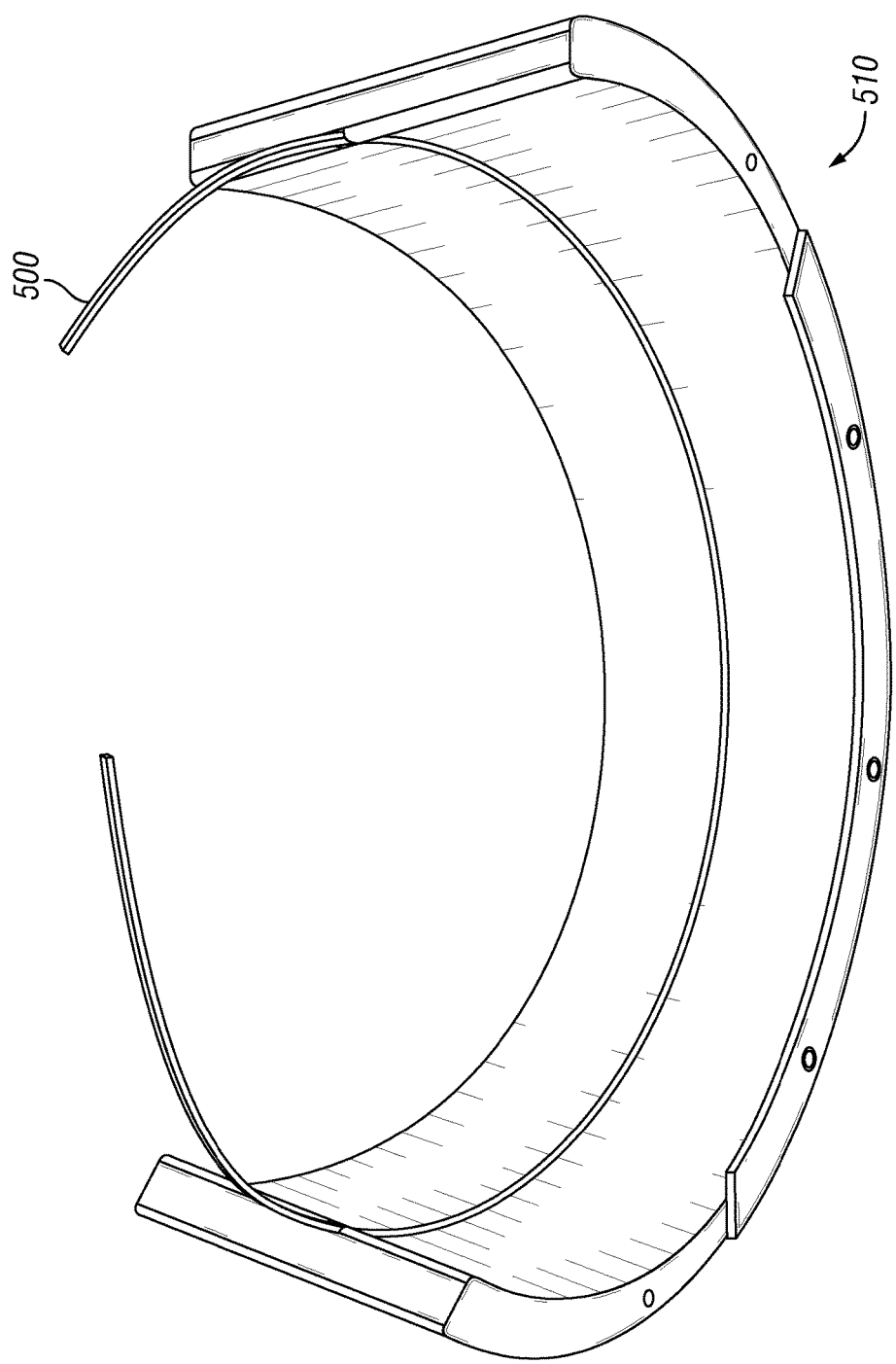
FIG. 23 shows a wire-in-slot assembly incorporating the FQI of FIG. 22.

Now referring to FIGS. 22 and 23, another exemplary category of FQIs may be provided in embodiments other than a flat ferrous or non-ferrous member. For example, an exemplary FQI as shown in FIG. 22 may include a single strand cable 500 with one or more small notches 502 cut along a length thereof. In this embodiment, a holder may be employed not only to ensure a repeatable placement of notch 502 in the cable's axis of rotation but also to ensure that the cable moves repeatedly parallel to the sensor array. For example, wire 500 may be employed as part of a wire-in-slot assembly 510 as shown in FIG. 23.

Example

Figure 24:
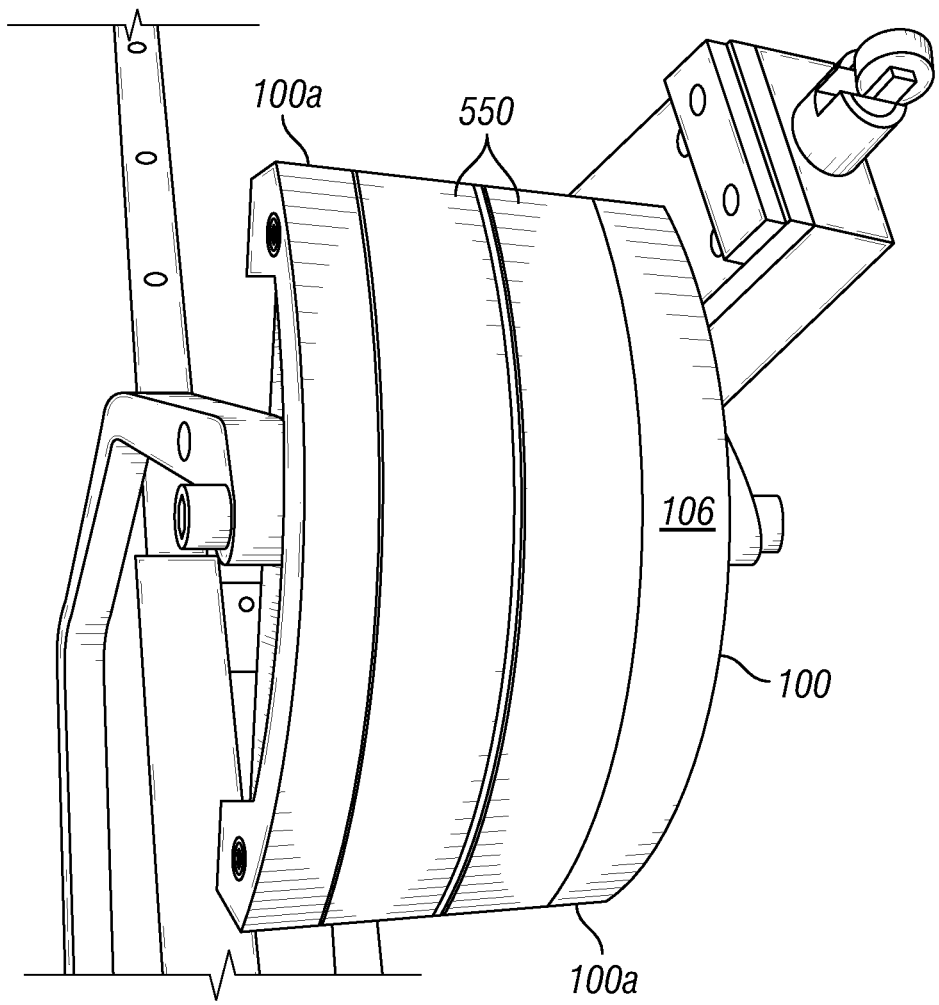
FIG. 24 show a front perspective view of an exemplary wire tape guide as used with an exemplary sensor inspection device for use with the FQI of FIG. 22.

An FQI is provided as a piece of wire with a notch, wherein the wire and the notch have the following parameters:
Wire Dimensions: 1.2 mm diameter×343 mm long
Notch Dimension: 0.6 mm deep×1.2 mm
Cross-sectional area of Notch: 50.0%
Average Peak-to-Peak Amplitude: 0.274 volts
Average Peak-to-Peak run to run variability: 0.014 volts The test method was very similar to that performed with respect to other FQIs formed as bars and plates (as disclosed herein), except that the wire was drawn across the sensor array in the opposite direction. The wire notch was placed just off the sensor on the bottom side and pulled up to the top of the sensor. Care was exercised to keep the wire inside a tape guide 550 as shown in FIG. 24 and pressed flush with the inspection surface 106 of sensor device 100.

Figure 25:
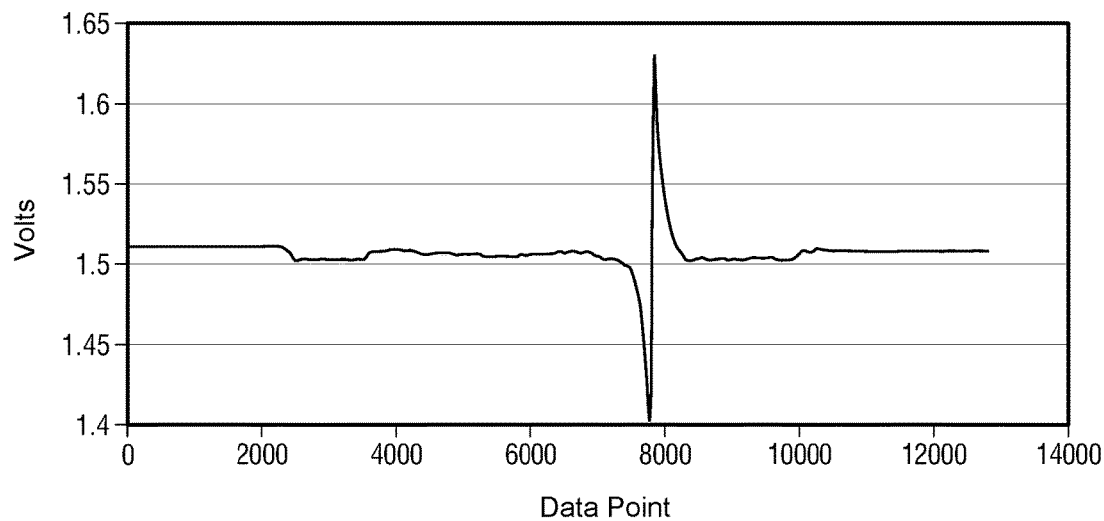
FIGS. 25 to 27 show exemplary comparisons of peak-to-peak values as an index of the exemplary FQI of FIG. 22 passes over a respective sensor of the exemplary sensor inspection device.
Figure 26:
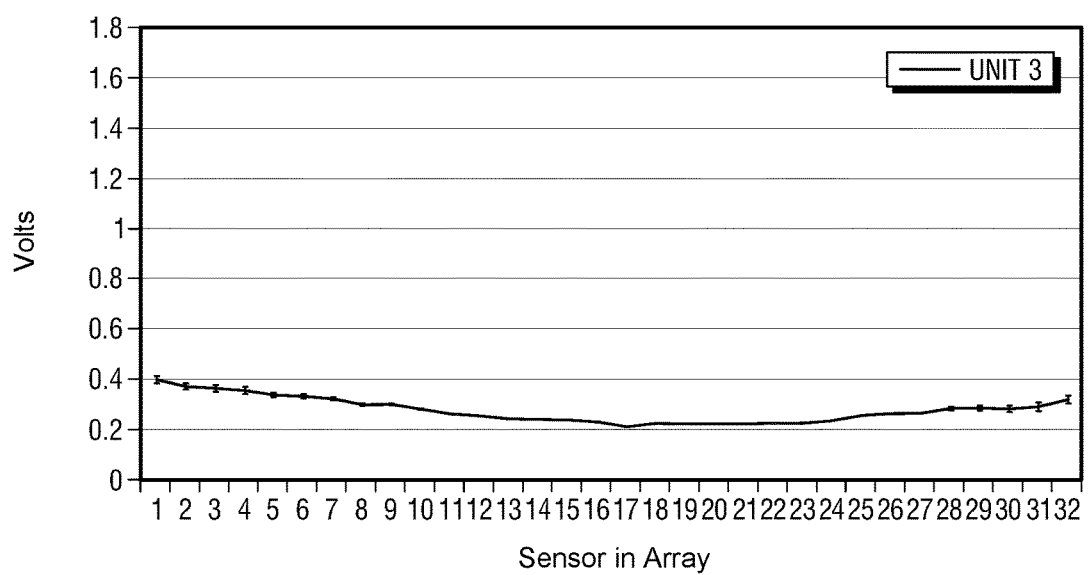

The signature of the wavelet is opposite from what is expected due to the reversed test method of starting at the bottom sensor and moving to the top (see FIG. 25). This is not an issue in extracting the peak-to-peak value but may present an issue in validating the magnet pole versus the sensor array orientation. Repeatability was excellent, especially in the middle of the sensor array (see FIG. 26).

Example

The wire of the previous example was embedded in a groove inside an aluminum arc of the proper inside diameter to produce an assembly such as assembly 510 shown in FIG. 23. The wire notch was located approximately in the middle of the arc circumferentially. A piece of Teflon tape was used to hold the wire in place and aid in sliding it over inspection surface 106 of sensor device 100. Tests were performed on all of the available sensors. A guide plate was bolted onto one side of the aluminum arc to aid in maintaining the center of sensor body 110.

Figure 27:
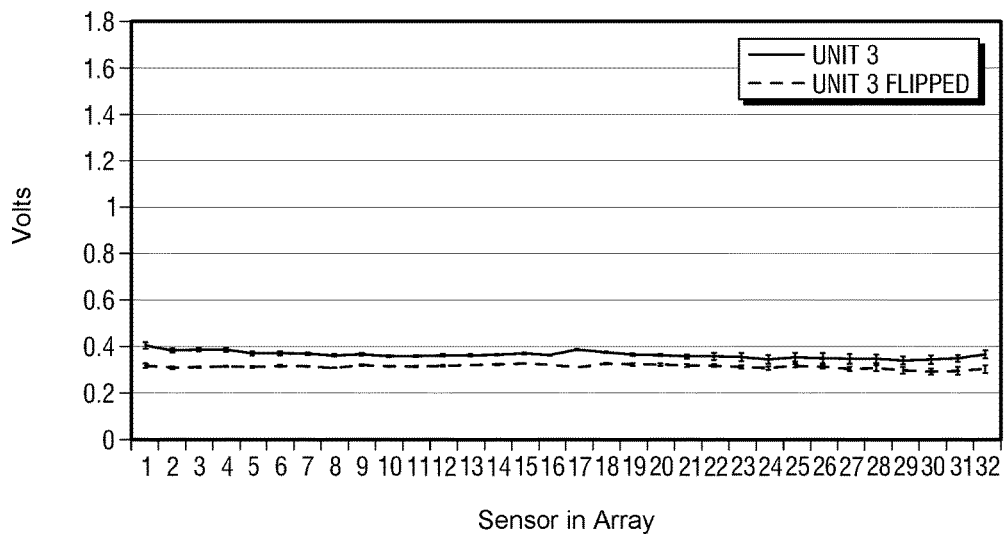

Tests were performed with the FQI flipped, essentially placing the guide plate on the opposite side of the sensor. From the plot shown in FIG. 27, it appears that there is a step change upon flipping. This is most likely due to the cable not being passed perfectly centered over the sensor array. The flux leakage should be detected the strongest directly over the senor array.

Repeatability with all tests was very good. A possible drawback to the single cable approach may be the need to be perfectly centered over the sensor array. With the sensor device placed in the tire, a slightly off-centered array should not pose a problem. When testing with this FQI, however, an offset may cause the sensor to provide a different measure of the flux leakage, resulting in the appearance of a sensor that is out of tolerance.

As disclosed herein, a simple test apparatus is provided that has good repeatability and provides a sensor response close to the working range of the sensor array during in situ tire testing. The typical response of a sensor device or system as disclosed herein is between 0.03 and 0.15 volts, representing the flux leakage from a discontinuity. The intensity of flux leakage from an index (notch, aperture, groove, slot or otherwise) is dependent on the overall loss of cross-sectional area and the separation between index edges. One primary factor appears to be the cross-sectional area. To aid in automatic wavelet extraction, a clearly defined wavelet is needed. This may require greater amplitude than the typical response of the sensor system.

Figure 28:
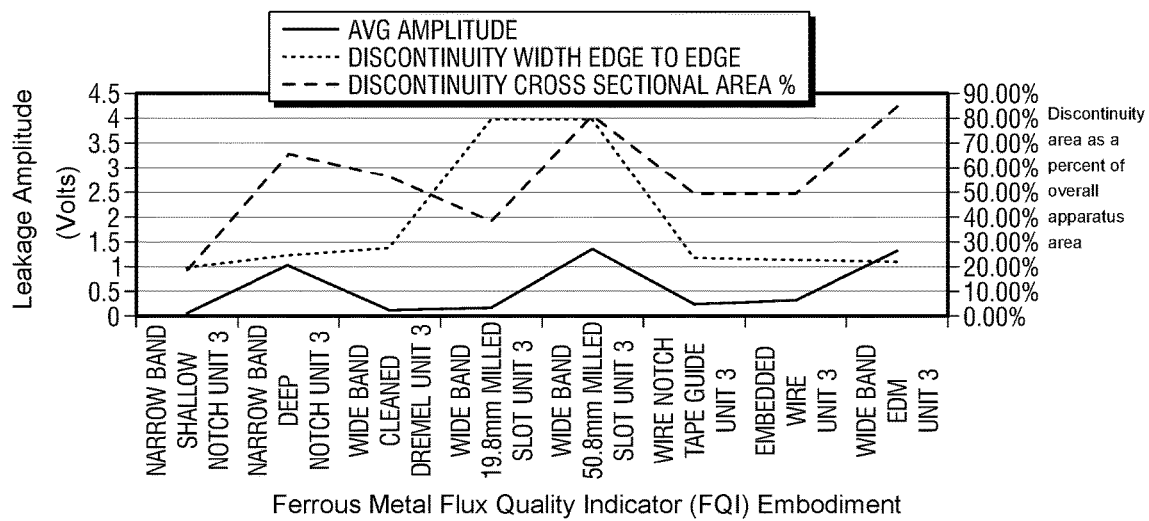
FIG. 28 shows an exemplary relationship of leakage amplitude in volts to edge-to-edge width of an index and the index cross-sectional area expressed as a percent of the overall apparatus cross-sectional area.

FIG. 28 indicates a relationship of the leakage amplitude in volts (left axis) to the edge-to-edge width of the discontinuity in millimeters (left axis) and the discontinuity cross-sectional area expressed as a percent of the overall apparatus cross-sectional area (right axis). The average amplitude is the average of each sensor's data for each test. All sensors (e.g., all 32 Hall Effect sensors) are then averaged together to obtain one value per FQI embodiment. From this data, it is advantageous to maintain an index cross-sectional area below 40% of the overall FQI cross-sectional area.

Figure 29:
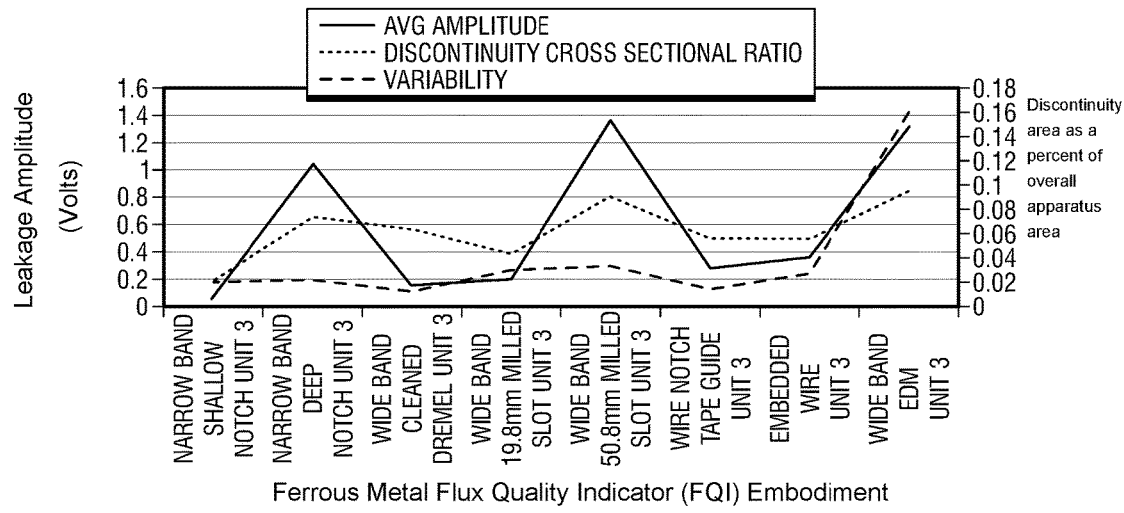
FIG. 29 shows exemplary repeatability of the exemplary FQIs disclosed herein.

FIG. 29 indicates the repeatability of each FQI embodiment. The amplitude is calculated the same as in the previous graph (left axis). The variability is the average of each sensor's maximum amplitude less the minimum amplitude for each FQI test. All sensors are then averaged together to obtain one value (right axis). The discontinuity cross-sectional ratio is the same as in the previous graph but plotted as a decimal instead of a percentage. It appears that if the cross-sectional area of the index is too large, it negatively affects the repeatability. When the percentage gets too large, it causes a dramatic increase in repeatability error.

Figure 30:
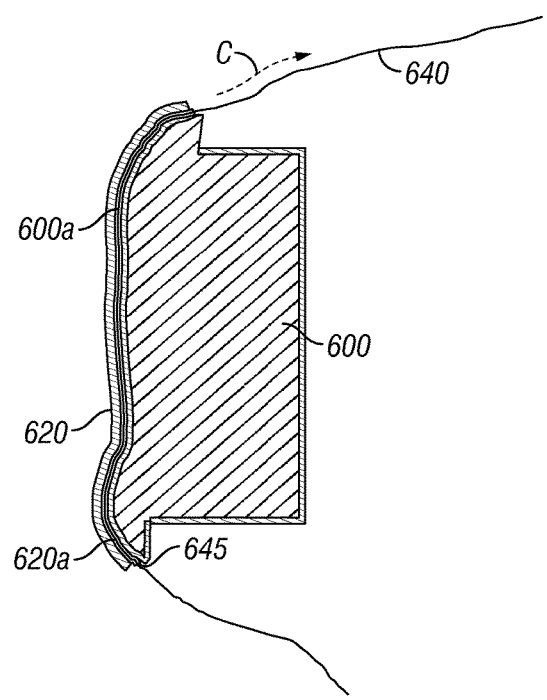
FIG. 30 shows a schematic side view of an exemplary bead sensor device for use with one or more FQIs as disclosed herein.

It is understood that the presently disclosed FQIs are amenable to use with sensor devices and sensor device systems that are used along regions of tires of various sizes and profiles. While the presently disclosed examples were performed with respect to single radius shoulder sensors disposed on a large sensor head, the same principles are applicable to determine flux leakage quality with respect to bead inspection devices and systems. As shown in FIG. 30, an exemplary bead sensor device 600 is shown that incorporates a sensor array. A guide 620 is provided with a groove 620a that is disposed adjacent an inspection surface 600a of bead sensor 600. An FQI is provided as an embedded wire 640 having a notch 645 incorporated therewith. Embedded wire 640 may exhibit a substantial channel shape that complements the complex shape of the bead sensor. Wire 640 may be "drawn" through groove 620 (for example, in the direction of arrow C in FIG. 30), thereby passing notch 645 over each of the sensors of the array in the same manner as described hereinabove. Data can be obtained in substantially the same manner as presently described herein.

At least some of the various techniques described herein may be implemented in connection with hardware or software or, where appropriate, with a combination of both. For example, electrical data processing functionality may be used to implement any aspect of signal derivation and peak-to-peak computation, including implementation in connection with a computing device (including a mobile networking apparatus) that includes hardware, software, or, where appropriate, a combination of both. The processing functionality may correspond to any type of computing device that includes one or more processing devices. The computing device can include any type of computer, computer system or other programmable electronic device, including a client computer, a server computer, a portable computer (including a laptop and a tablet), a handheld computer, a mobile phone (including a smart phone), a gaming device, an embedded controller, a near-field communication device, a device with applications implemented at least partly using a cloud service, and any combination and/or equivalent thereof (including touchless devices). Moreover, the computing device may be implemented using one or more networked computers, e.g., in a cluster or other distributed computing system. The network may be a LAN, a WAN, a SAN, a wireless network, a cellular network, radio links, optical links and/or the Internet, although the network is not limited to these network selections.

A server may be further configured to facilitate communication between one or more FQIs as disclosed herein and one or more of the computing devices. A database may be built and accessed that includes stored data and calculated data that can be generated for intended flux leakage integrity. Test data may be uploaded through the server and stored on the database for calculating and comparing these with stored flux leakage quantities. One or more representations of the calculated and/or compared data may be generated and optionally displayed on a user interface.

The presently disclosed subject matter may complement any device that can be properly positioned proximate a tire surface to facilitate inspection of the tire. Such devices can be used to repeatedly place one or more sensors (and one or more sensor types) at the inner surface of various tires, including along the shoulder regions. Magnetic flux sensor quality indicators and methods as presently disclosed therefore enable reliable use of sensors for a wide range of tire profiles and widths.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Also, the dimensions and values disclosed herein are not limited to a specified unit of measurement. For example, dimensions expressed in English units are understood to include equivalent dimensions in metric and other units (e.g., a dimension disclosed as "1 inch" is intended to mean an equivalent dimension of "2.5 cm").

As used herein, the term "method" or "process" refers to one or more steps that may be performed in other ordering than shown without departing from the scope of the presently disclosed invention. As used herein, the term "method" or "process" may include one or more steps performed at least by one electronic or computer-based apparatus. Any sequence of steps is exemplary and is not intended to limit methods described herein to any particular sequence, nor is it intended to preclude adding steps, omitting steps, repeating steps, or performing steps simultaneously. As used herein, the term "method" or "process" may include one or more steps performed at least by one electronic or computer-based apparatus having a processor for executing instructions that carry out the steps.

The terms "a," "an," and the singular forms of words shall be taken to include the plural form of the same words, such that the terms mean that one or more of something is provided. The terms "at least one" and "one or more" are used interchangeably. Ranges that are described as being "between a and b" are inclusive of the values for "a" and "b."

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the disclosed apparatus have been illustrated and described, it will be understood that various changes, additions and modifications can be made without departing from the spirit and scope of the present disclosure. Accordingly, no limitation should be imposed on the scope of the presently disclosed invention, except as set forth in the accompanying claims.

What is claimed is:

1. A flux leakage detection system, comprising:
   a ferrous metal flux quality indicator (FQI) having at least one index incorporated between two opposed extents thereof that approximates an anomaly in metallic tissue with the at least one index having a cumulative cross-sectional area to facilitate flux leakage from ferrous metal;
   a sensor inspection device for detecting breaks in ferrous reinforcement elements during a tire inspection process, with the sensor inspection device having a permanent magnet to create fields of magnetic flux used in detecting breaks in ferrous reinforcements during the tire inspection process, wherein the sensor inspection device having a sensor array having a plurality of sensors spaced from one another along a path, wherein the sensor inspection device having a curved sensor inspection surface that engages the FQI during data collection, wherein the sensors of the sensor array are located between the permanent magnet and the sensor inspection surface;
   wherein movement of the FQI is effected such that, at the start of a test, the at least one index is disposed between one magnetic pole of the magnet and one end of the sensor array of the sensor inspection device; and
   once data collection has started, movement of the FQI is effected such that the at least one index is moved relative to the sensor array at a constant speed along a curvilinear path past the sensors of the sensor array one after another until the index is disposed between an opposite end of the sensor array and an opposite magnetic pole of the magnet.

2. The flux leakage detection system of claim 1, wherein the sensor inspection device includes a body having the inspection surface that is an outermost surface of the body and the sensors selected from the group consisting of one or more Hall Effect sensors, temperature sensors, optical sensors and combinations thereof.

3. The flux leakage detection system of claim 2, wherein the outermost inspection surface exhibits a profile of an arc of a circle having a predefined radius of curvature and movement of the index is effected curvilinearly relative to the sensor array during data collection.

4. The flux leakage detection system of claim 3, wherein the at least one index includes at least one of one or more notches, grooves, apertures and slots integral with a surface of the FQI proximate the sensor inspection device during data collection and the at least one index is optionally coextensive with the opposed sides of the bar and approximately equidistant between the opposed extents of the bar.

5. The flux leakage detection system of claim 4, wherein the FQI is fabricated as one of:
   an essentially flat metal bar that conforms to the outermost inspection surface and has a predetermined width, a predetermined thickness and a pair of opposed sides of predetermined length coextensive with a pair of opposed extents and delineating the predetermined width; and
   a single strand cable that conforms to the outermost inspection surface, the cable having a pair of opposed extents and a predetermined length along which the at least one index is disposed, wherein a holder is selectively provided that ensures repeatable parallel movement of the cable along a length of the sensor array.

6. The flux leakage detection system of claim 5, wherein the predetermined length of the bar is selected from:
   a length equal to or less than a curvilinear distance between the two magnetic poles of the sensor inspection device; and
   a length sufficient such that, when at least a portion of the FQI is moved between opposed ends of an array of flux sensors of the sensor inspection device, neither opposed end of the FQI leaves a magnetic pole of the sensor inspection device.

7. The flux leakage detection system of claim 6, wherein the at least one index comprises at least one of:

at least one notch of predetermined depth relative to the predetermined width and the predetermined length of the bar, and the predetermined depth is deep enough to provide a recognizable flux leakage wavelet; and an aperture extending through the predetermined thickness of the bar and optionally equidistant from the opposed sides.

8. A method for providing a quality indicator for a flux leakage detection system, comprising:

providing a flux leakage detection system according to claim 1;

moving the FQI such that, at the start of a test, the at least one index is disposed between one magnetic pole of the magnet and one end of a sensor array of the sensor inspection device; and once data collection has started, moving the index relative to the sensor array at a constant speed along a curvilinear path past the sensors of the sensor array one after another until the at least one index is disposed between an opposite end of the sensor array and an opposite magnetic pole of the magnet.

9. The method of claim 8, further comprising providing the sensor inspection device with a body having the inspection surface that is an outermost surface of the body and the sensors selected from the group consisting of one or more Hall Effect sensors, temperature sensors, optical sensors and combinations thereof.

10. The method of claim 9, wherein the outermost inspection surface exhibits a profile of an arc of a circle having a predefined radius of curvature such that movement of the at least one index is effected curvilinearly relative to the sensor array during data collection.

11. The method of claim 10, wherein the at least one index includes at least one of one or more notches, grooves, apertures and slots integral with a surface of the FQI proximate the sensor inspection device during data collection, and the at least one index is optionally coextensive with the opposed sides of the bar and approximately equidistant between the opposed extents of the bar.

12. The method of claim 11, further comprising fabricating FQI as one of:

an essentially flat metal bar that conforms to the outermost inspection surface and has a predetermined width, a predetermined thickness and a pair of opposed sides of predetermined length coextensive with a pair of opposed extents and delineating the predetermined width; and a single strand cable that conforms to the outermost inspection surface, the cable having a pair of opposed extents and a predetermined length along which the at least one index is disposed, wherein a holder is selectively provided that ensures repeatable parallel movement of the cable along a length of the sensor array.

13. The method of claim 12, wherein the predetermined length of the bar is selected from:

a length equal to or less than a curvilinear distance between the two magnetic poles of the sensor inspection device; and a length sufficient such that, when at least a portion of the FQI is moved between opposed ends of the array of flux sensors of the sensor inspection device, neither opposed end of the FQI leaves a magnetic pole of the sensor inspection device.

14. The method of claim 13, wherein the at least one index comprises at least one of:

at least one notch of predetermined depth relative to the predetermined width and the predetermined length of the bar, and the predetermined depth is deep enough to provide a recognizable flux leakage wavelet; and an aperture or slot extending through the predetermined thickness of the bar and optionally equidistant from the opposed sides.

15. The method of claim 8, further comprising providing one or more network-connected computing devices in communication with at least one of the FQI and the sensor inspection device, wherein the one or more network-connected computing devices include instructions for performing at least one of transferring data from at least one of the FQI and the sensor inspection device and controlling one or both of the FQI and the sensor inspection device either directly or indirectly.

16. The method of claim 15, further comprising providing a platform including at least one of:

a server in communication with at least one network-connected device with the server configured to perform actions comprising at least one of:

communicating over a network;

facilitating communication between the at least one network-connected device and the one or more computing devices;

building and accessing a database of stored peak-to-peak response values that can be generated for intended flux leakage integrity, wherein the stored peak-to-peak response values are representative of flux leakage integrity of previously tested sensors;

uploading test data for storage on the database; and generating one or more representations of one or more of the peak-to-peak response values; and an engine configured to perform at least one of:

recording test data as each sensor inspection device is tested;

recording high peaks and low peaks of each sensor as the at least one index is moved thereover;

computing peak-to-peak response values as the at least one index passes over each sensor;

comparing a peak-to-peak response value of at least one sensor with at least one other peak-to-peak response value; and based upon the comparing, determining flux leakage integrity.

17. The flux leakage detection system of claim 1, further comprising one or more network-connected computing devices in communication with at least one of the FQI and the sensor inspection device, wherein the one or more network-connected computing devices include instructions for performing at least one of transferring data from at least one of the FQI and the sensor inspection device and controlling one or both of the FQI and the sensor inspection device either directly or indirectly.

18. The flux leakage detection system of claim 17, further comprising a platform including at least one of:

a server in communication with at least one network-connected device with the server configured to perform actions comprising at least one of:

communicating over a network;

facilitating communication between the at least one network-connected device and the one or more computing devices;

building and accessing a database of stored peak-to-peak response values that can be generated for intended flux leakage integrity, wherein the stored peak-to-peak response values are representative of flux leakage integrity of previously tested sensors;

uploading test data for storage on the database; and generating one or more representations of one or more of the peak-to-peak response values; and an engine configured to perform at least one of:

recording test data as each sensor inspection device is tested;

recording high peaks and low peaks of each sensor as the at least one index is moved thereover;

computing peak-to-peak response values as the at least one index passes over each sensor;

comparing a peak-to-peak response value of at least one sensor with at least one other peak-to-peak response value; and based upon the comparing, determining flux leakage integrity.

\* \* \* \* \*